United States Patent
Horos et al.

(10) Patent No.: US 12,421,542 B2
(45) Date of Patent: Sep. 23, 2025

(54) ADVANCED DUMBELL PCR FOR ISOMIR DETECTION

(71) Applicant: Hummingbird Diagnostics GmbH, Heidelberg (DE)

(72) Inventors: Rastislav Horos, Heidelberg (DE); Bruno Steinkraus, Hanstedt (DE); Carla Bieg-Salazar, Heidelberg (DE)

(73) Assignee: Hummingbird Diagnostics GmbH, Heidelberg (DE)

( * ) Notice: Subject to any disclaimer, the term of this patent is extended or adjusted under 35 U.S.C. 154(b) by 0 days.

(21) Appl. No.: 18/160,542

(22) Filed: Jan. 27, 2023

(65) Prior Publication Data
US 2023/0313284 A1 Oct. 5, 2023

Related U.S. Application Data

(63) Continuation of application No. PCT/EP2022/072077, filed on Aug. 5, 2022.

(30) Foreign Application Priority Data

Aug. 11, 2021 (EP) .................................. 21190781
Aug. 5, 2022 (WO) .................. PCT/EP2022/072077

(51) Int. Cl.
*C12Q 1/6855* (2018.01)
(52) U.S. Cl.
CPC ................. *C12Q 1/6855* (2013.01)
(58) Field of Classification Search
None
See application file for complete search history.

(56) References Cited

U.S. PATENT DOCUMENTS

| 5,399,676 A * | 3/1995 | Froehler ............... C12N 15/113 536/28.4 |
| 9,528,107 B2 | 12/2016 | Pham et al. |
| 2018/0251830 A1* | 9/2018 | Kirino .................. C12Q 1/6853 |
| 2020/0255824 A1 | 8/2020 | Lai et al. |

FOREIGN PATENT DOCUMENTS

| WO | 2012/103154 A1 | 8/2012 |
| WO | 2021/148717 A1 | 7/2021 |

OTHER PUBLICATIONS

Desingu, Dumbbell-PCR: Blocking the 3' end of 3' Db-adapter is expected to avoid non specific detection and increase the efficacy of this method, 2015—Comment accompanying Honda, Dumbbell-PCR . . . Nucleic Acids Research, 43(12): 1-12, 2015. (Year: 2015).*
International Search Report in PCT/EP2022/072077, mailed Dec. 13, 2022, 15 pages.
Honda et al. Dumbbell-PCR: a method to quantify specific small RNA variants with a single nucleotide resolution at terminal sequences. Nucleic acids research. Jul. 13, 2015;43(12):e77-.
Yu et al. Nanoliter droplet array for microRNA detection based on enzymatic stem-loop probes ligation and SYBR Green real-time PCR. Talanta. Sep. 30, 2011;85(4):1760-5.
Mei, et al. "A facile and specific assay for quantifying microRNA by an optimized RT-qPCR approach." (2012): e46890.
Office Action in JP 2023-521142, mailed Jan. 10, 2024, 6 pages.

* cited by examiner

Primary Examiner — Gary Benzion
Assistant Examiner — Carolyn L Greene
(74) Attorney, Agent, or Firm — Kilpatrick Townsend & Stockton LLP

(57) ABSTRACT

The present invention relates to a method for the detection of small non-coding RNAs in a sample using sequence-specific structured adapters for the ligation by a double stranded RNA ligase with subsequent cDNA production and quantification. The present invention further relates to a kit for carrying out this method.

14 Claims, 6 Drawing Sheets

Specification includes a Sequence Listing.

FIGURE 1

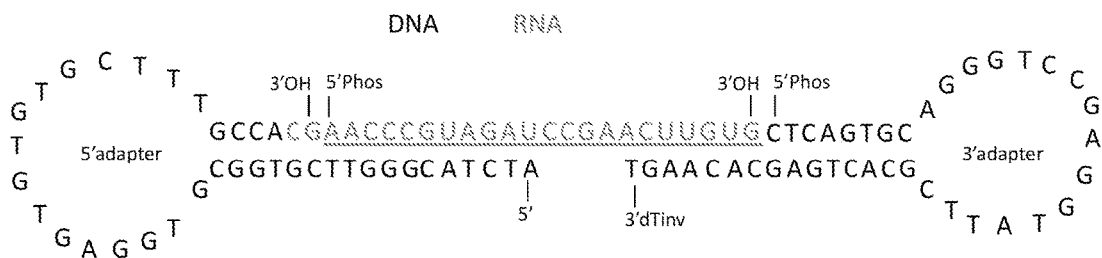

Characteristics of the 5' adapter (5' ATCTACGGGTT<u>CGTGGC</u>GTGGAGTGTGTGCTTT<u>GCCArCrG</u> 3' (SEQ ID NO: 6)):
- a stem loop structure formed by the loop and double stranded stem
- a 5' single stranded protrusion that is reverse complementary to the 5' end of the RNA target; length can be 6 to 15 nucleotides
- at least two ribonucleotides at the 3' end of the polynucleotide
- locked nucleotide- (LNA-) enhanced sequence (not indicated in Figure 1)

Characteristics of the 3' adapter (5' /5Phos/<u>CTCAGTGC</u>AGGGTCCGAGGTATTC<u>GCACTGAG</u>CACAAGT/3InvdT/ 3' (SEQ ID NO: 7)):
- a stem loop structure formed by the loop and double stranded stem
- a 3' single stranded protrusion that is reverse complementary to the 3' end of target RNA; length can be 6 to 15 nucleotides
- a 5' phosphor moiety
- an inverted dT modification on 3' end of the polynucleotide
- locked nucleotide- (LNA-) enhanced sequence (not indicated in Figure 1)

target RNA: miR-100-5p (5' AACCCGUAGAUCCGAACUUGUG 3' (SEQ ID NO: 8))

FIGURE 3

| Adapter combination specific for | RNA template ||||||||
|---|---|---|---|---|---|---|---|---|
| | miR-100-5p | miR-100-5p 5' Del | miR-100-5p 5' Add | miR-100-5p 3' Del | miR-100-5p 3' Add | miR-100-5p Seed Mut. | miR-100-5p Mid Mismatch | miR-100-5p 3' Mismatch |
| miR-100-5p | 15.59 | | 18.28 | 18.31 | 19.23 | | | 22.46 |
| miR-100-5p 5' Del | 24.23 | 26.93 | | | | | | |
| miR-100-5p 5' Add | | | 20.70 | | | | | |
| miR-100-5p 3' Del | | | | 19.81 | | | | |
| miR-100-5p 3' Add | 18.75 | | | 24.45 | 16.41 | | | |
| miR-100-5p Seed Mut. | 28.71 | | | 27.50 | 22.38 | 18.71 | | |
| miR-100-5p Mid Mismatch | 31.13 | | | | | | 18.03 | |
| miR-100-5p 3' Mismatch | 16.88 | | 22.85 | 22.49 | 23.05 | | | 16.70 |

(signal expected / signal not expected)

FIGURE 4

| miR-100-5p | AACCCGUAGAUCCGAACUUGUG | SEQ ID NO: 8 |
|---|---|---|
| miR-100-5p 5' Del | -ACCCGUAGAUCCGAACUUGUG | SEQ ID NO: 9 |
| miR-100-5p 5' Add | AAACCCGUAGAUCCGAACUUGUG | SEQ ID NO: 10 |
| miR-100-5p 3' Del | AACCCGUAGAUCCGAACUUGU- | SEQ ID NO: 11 |
| miR-100-5p 3' Add | AACCCGUAGAUCCGAACUUGUGG | SEQ ID NO: 12 |
| miR-100-5p Seed Mut. | AACGCGUAGAUCCGAACUUGUG | SEQ ID NO: 13 |
| miR-100-5p Mid Mismatch | AACCCGUAGAUGCGAACUUGUG | SEQ ID NO: 14 |
| miR-100-5p 3' Mismatch | AACCCGUAGAUCCGAACUAGUG | SEQ ID NO: 15 |

FIGURE 6

| Oligo name | Sequence 5'->3' | SEQ ID: | Purpose |
|---|---|---|---|
| DB-mir100-5A | ATCTACGGGTTCGTGGCG/idSp/TGGAGTGTGTGCTTTGCCArCrG | 16 | 5'adapter for ligation |
| DB-mir100-5B | GATCTACGGGTCGTGGCG/idSp/TGGAGTGTGTGCTTTGCCArCrG | 17 | 5'adapter for ligation |
| DB-mir100-5D | TCTACGGGTTTCGTGGCG/idSp/TGGAGTGTGTGCTTTGCCArCrG | 18 | 5'adapter for ligation |
| DB-mir100-5E | ATCTACGCGTTCGTGGCG/idSp/TGGAGTGTGTGCTTTGCCArCrG | 19 | 5'adapter for ligation |
| DB-mir100-3Z | /5Phos/CTCAGTGCAGGGTCCGAGGTATTCGCACTGAGCACAAGT/3InvdT/ | 20 | 3'adapter for ligation |
| DB-mir100-3X | /5Phos/CTCAGTGCAGGGTCCGAGGTATTCGCACTGAGACAAGTT/3InvdT/ | 21 | 3'adapter for ligation |
| DB-mir100-3S | /5Phos/CTCAGTGCAGGGTCCGAGGTATTCGCACTGAGCCACAAG/3InvdT/ | 22 | 3'adapter for ligation |
| DB-mir100-3T | /5Phos/CTCAGTGCAGGGTCCGAGGTATTCGCACTGAGCACTAGT/3InvdT/ | 23 | 3'adapter for ligation |
| DB-mir100-K | /56-FAM/ACGAACCCG/ZEN/TAGATCCGAAC/3IABkFQ/ | 24 | Taqman probe |
| DB-mir100-L | /56-FAM/ACGACCCGT/ZEN/AGATCCGAACT/3IABkFQ/ | 25 | Taqman probe |
| DB-mir100-P | /56-FAM/ACGAAACCC/ZEN/GTAGATCCGAA/3IABkFQ/ | 26 | Taqman probe |
| DB-mir100-Q | /56-FAM/ACGAACGCG/ZEN/TAGATCCGAAC/3IABkFQ/ | 27 | Taqman probe |
| DB-mir100-R | /56-FAM/ACGAACCCG/ZEN/TAGATGCGAAC/3IABkFQ/ | 28 | Taqman probe |
| DB-RT | CTCAGTGCGAATACCTCGGACCCT | 3 | reverse transcription primer |
| DB-PCR-F | TGGAGTGTGTGCTTTGCCACG | 4 | forward primer for pre-amplification and qPCR |
| DB-PCR-R | GTGCGAATACCTCGGACC | 5 | reverse primer for pre-amplification and qPCR |

FIGURE 7

| Variant | 5'adapter | 3'adapter | Taqman probe |
|---|---|---|---|
| miR-100-5p | DB-mir100-5A | DB-mir100-3Z | DB-mir100-K |
| miR-100-5p 5' Del | DB-mir100-5B | DB-mir100-3Z | DB-mir100-L |
| miR-100-5p 5' Add | DB-mir100-5D | DB-mir100-3Z | DB-mir100-P |
| miR-100-5p 3' Del | DB-mir100-5A | DB-mir100-3X | DB-mir100-K |
| miR-100-5p 3' Add | DB-mir100-5A | DB-mir100-3S | DB-mir100-K |
| miR-100-5p Seed Mut. | DB-mir100-5E | DB-mir100-3Z | DB-mir100-Q |
| miR-100-5p Mid Mismatch | DB-mir100-5A | DB-mir100-3Z | DB-mir100-R |
| miR-100-5p 3' Mismatch | DB-mir100-5A | DB-mir100-3T | DB-mir100-K |

ADVANCED DUMBELL PCR FOR ISOMIR DETECTION

CROSS REFERENCE TO RELATED APPLICATIONS

This application is a Continuation of PCT/EP2022/072077, International Filing Date 5 Aug. 2022 which is claims priority to EP 21190781.1 filing date 11 Aug. 2021, the disclosures of each are incorporated herein by reference for all purposes.

REFERENCE TO A SEQUENCE LISTING

The instant application contains a Sequence Listing which has been submitted electronically in XML format. Said XML copy, created on Feb. 27, 2023, is named 095697-1370468-005000US.xml and is 72,849 bytes in sizes, is herein incorporated by reference in its entirety.

The present invention relates to a method for the detection of small non-coding RNAs in a sample using sequence-specific structured adapters for the ligation by a double stranded RNA ligase with subsequent cDNA production and quantification. The present invention further relates to a kit for carrying out this method.

BACKGROUND OF THE INVENTION

Non-protein-coding regions of the genome are widely transcribed to produce small non-coding RNAs such as miRNAs which play crucial roles in normal biological processes and disease states. The diversity and expression of these small non-coding RNAs such as miRNAs can, thus, be used for diagnostic purposes.

Next generation sequencing (NGS) methods are able to detect an immense range of small non-coding RNAs such as miRNAs and are, therefore, primarily used for discovery purposes. Yet, the usage of NGS is connected with increased run-to-run and lab-to-lab variability and cannot be accommodated in most of the diagnostic laboratories due to its massive costs. Nevertheless, NGS is a powerful tool to create profiles of small non-coding RNAs such as miRNAs that can be used for disease prediction.

In view of the above, there is a need to develop an orthogonal method for the detection and quantification of small non-coding RNAs such as miRNA and to validate the NGS data that can be used in a wide range of labs in a cost-effective manner.

Two main methods for the detection and quantification of miRNAs are being currently used. The first method uses a stem-loop like probe hybridizing to the 3' end of miRNAs, followed by a reverse transcription (RT) reaction and quantitative polymerase chain reaction (qPCR) detection using a forward, miRNA-specific, primer and a reverse primer hybridizing to the probe (e.g. classic miRNA TaqMan assay). In a second method, a poly-A tailing reaction is applied first, creating a stretch of adenins at the 3' end of the miRNAs, followed by the RT using oligo-d(T) primer. Subsequently, a miRNA-specific forward primer is used together with a common reverse primer for qPCR reaction (e.g. miRCury LNA assays, etc.).

The common problem of the above methods is that the miRNA-specific forward primers are unable to discriminate variations of the sequence at the 5' end of miRNAs (e.g. additions, deletions, mutations) and at the 3' end of miRNAs (e.g. additions). As a result, the final processed RNA sequencing data do not accurately reflect the underlying biological situation. Thus, the isomiR specific information, as discovered by NGS, cannot be faithfully validated by currently available qPCR methods. Due to the diversity of the miRNA variants at both 3' and 5' ends, a hybridization-based method has by definition a low potential to capture and quantify the exact isomiR of interest.

Thus, there is a further need to develop a method which not only allows the detection and quantification of miRNAs but also of isomiRs in a fast, reliable and precise manner. In addition, this method should allow the detection and quantification of miRNAs but also of isomiRs with high specificity and sensitivity and, thus, improve diagnosis and/or prognosis of diseases.

Moreover, there is a further need to develop a kit suitable for the above purpose for use at any hospital/clinical or research center.

The present inventors have developed a Dumbbell PCR (DB PCR) based method, which exploits the ability of a double stranded RNA ligase, particularly RNA ligase 2 (Rnl2), to specifically join the nicks in hybridized double stranded RNA molecule. Only correctly hybridized adaptors both to the 5' and the 3' end of the isomiRs enable the formation of the ligated RNA that can be used as template for cDNA synthesis. This method is able to specifically and efficiently determine and quantify the expression of target RNA (e.g. miRNA) as well as of target RNA variants having specific terminal sequences (e.g. isomiR). Second layer of specificity is introduced by a TaqMan probe, that can align to a user-defined region of cDNA sequence. The Dumbbell PCR (DB PCR) based method developed by the present inventors can be used at any hospital/clinical or research center and allows the analysis of clinical samples in a simple, fast, reliable, precise, and cost-effective manner. Due to this method, the specificity and sensitivity of a diagnostic tests can further be improved. A kit suitable for the above purpose is also provided.

SUMMARY OF THE INVENTION

In a first aspect, the present invention relates to a 5' adapter comprising in the following order from 5' to 3'
 (i) a 5' terminal nucleotide sequence comprising 6 to 15 deoxynucleotides, wherein said 6 to 15 deoxynucleotides are reverse complementary to a 5'-terminal sequence of a target RNA, and
 (ii) a nucleotide sequence capable of forming a stem-loop structure containing a loop and a double stranded stem, wherein at least 2 nucleotides at its 3' end are ribonucleotides or modified ribonucleotides and wherein the nucleotide sequence is locked nucleotide-(LNA) enhanced.

In a second aspect, the present invention relates to a 3' adapter comprising in the following order from 5' to 3'
 (i) a nucleotide sequence capable of forming a stem-loop structure containing a loop and a double stranded stem, wherein the 5'-terminal nucleotide is phosphorylated and wherein the nucleotide sequence is locked nucleotide-(LNA-) enhanced, and
 (ii) a 3' terminal nucleotide sequence comprising 6 to 15 deoxynucleotides, wherein said 6 to 15 deoxynucleotides are reverse complementary to a 3'-terminal sequence of a target RNA and wherein the 3' terminal deoxynucleotide is an inverted deoxynucleotide.

In a third aspect, the present invention relates to a combination comprising
 the 5' adapter according to the first aspect, and
 the 3' adapter according to the second aspect.

In a fourth aspect, the present invention relates to a method of ligating two adapters to a target RNA in a sample comprising the steps of:
(i) providing a composition comprising a denatured target RNA in a sample, the renatured 5' adapter according to the first aspect, and the renatured 3' adapter according to the second aspect, wherein the 5' adapter and the 3' adapter are annealed to the target RNA, and
(ii) ligating the 5' adapter and the 3' adapter to the target RNA using/with a double stranded RNA ligase, thereby producing a ligation product.

In a fifth aspect, the present invention relates to a method of determining and/or quantifying a target RNA in a sample comprising the steps of:
(i) carrying out the method according to the fourth aspect,
(ii) reverse transcribing the ligation product, thereby obtaining a cDNA product from the target RNA, and
(iii) amplifying the cDNA, thereby determining and/or quantifying the target RNA.

In a sixth aspect, the present invention relates to a method of diagnosing a disease or condition in a patient comprising the steps of
(ia) carrying out the methods according to the third and/or fourth aspect, thereby determining the presence of the target RNA, and
(iia) diagnosing whether the patient is afflicted by the disease or condition based on the presence of the target RNA, or
(ib) carrying out the methods according to the third and/or fourth aspect, thereby quantifying the target RNA,
(iib) comparing the quantified target RNA with a reference, and
(iiib) diagnosing whether the patient is afflicted by the disease or condition based on the comparison.

In a seventh aspect, the present invention relates to a kit comprising
the 5' adapter according to the first aspect, and
the 3' adapter according to the second aspect, or
the combination according to the third aspect.

This summary of the invention does not necessarily describe all features of the present invention. Other embodiments will become apparent from a review of the ensuing detailed description.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kolbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention. In the event of a conflict between the definitions or teachings of such incorporated references and definitions or teachings recited in the present specification, the text of the present specification takes precedence.

The term "comprise" or variations such as "comprises" or "comprising" according to the present invention means the inclusion of a stated integer or group of integers but not the exclusion of any other integer or group of integers. The term "consisting essentially of" according to the present invention means the inclusion of a stated integer or group of integers, while excluding modifications or other integers which would materially affect or alter the stated integer. The term "consisting of" or variations such as "consists of" according to the present invention means the inclusion of a stated integer or group of integers and the exclusion of any other integer or group of integers.

The terms "a" and "an" and "the" and similar reference used in the context of describing the invention (especially in the context of the claims) are to be construed to cover both the singular and the plural, unless otherwise indicated herein or clearly contradicted by context.

The term "nucleotide", as used herein, refers to an organic molecule consisting of a nucleoside and a phosphate. In particular, a nucleotide is composed of three subunit molecules: a nucleobase, a five-carbon sugar (ribose or deoxyribose), and a phosphate group consisting of one to three phosphates. The four nucleobases in DNA are guanine, adenine, cytosine and thymine; in RNA, uracil is used in place of thymine. The nucleotide serves as monomeric unit of nucleic acid polymers, such as deoxyribonucleotide acid (DNA) or ribonucleotide acid (RNA). Thus, the nucleotide is a molecular building-block of DNA and RNA.

The term "nucleoside", as used herein, refers to a glycosylamine that can be thought of as nucleotide without a phosphate group. A nucleoside consists simply of a nucleobase (also termed a nitrogenous base) and a five-carbon sugar (ribose or 2'-deoxyribose) whereas a nucleotide is composed of a nucleobase, a five-carbon sugar, and one or more phosphate groups. In a nucleoside, the anomeric carbon is linked through a glycosidic bond to the N9 of a purine or the N1 of a pyrimidine.

The terms "nucleotide sequence" or "polynucleotide" are interchangeably used herein and refer to single-stranded and double-stranded polymers of nucleotide monomers, including without limitation, 2'-deoxyribonucleotides (DNA) and ribonucleotides (RNA) linked by internucleotide phosphodiester bond linkages, or internucleotide analogs, and associated counter ions, e.g., H+, NH4+, trialkylammonium, Mg2+, Na+, and the like. A nucleotide sequence or polynucleotide may be composed entirely of deoxyribonucleotides, entirely of ribonucleotides, or chimeric mixtures thereof and may include nucleotide analogs. The nucleotide monomer units may comprise any of the nucleotides described herein, including, but not limited to, nucleotides and/or nucleotide analogs.

The term "analog", as used herein, includes synthetic analogs having modified base moieties, modified sugar moieties, and/or modified phosphate ester moieties. Phosphate analogs generally comprise analogs of phosphate wherein the phosphorous atom is in the +5 oxidation state and one or more of the oxygen atoms is replaced with a non-oxygen moiety, e.g. sulfur. Exemplary phosphate analogs include: phosphorothioate, phosphorodithioate, phosphoroselenoate, phosphorodiselenoate, phosphoroanilothioate, phosphoranilidate, phosphoramidate, boronophosphates, including associated counterions, e.g. H+, NH4+, Na+. Exemplary base analogs include: 2,6-diaminopurine, hypoxanthine, pseudouridine, C-5-propyne, isocytosine, isoguanine, 2-thiopyrimidine. Exemplary sugar analogs include: 2'- or 3'-modifications where the 2'- or 3'-position is hydrogen, hydroxy, alkoxy, e.g., methoxy, ethoxy, allyloxy, isopropoxy, butoxy, isobutoxy and phenoxy, azido, amino or alkylamino, fluoro, chloro, and bromo.

In one embodiment, modified ribonucleotides are present in/part of the adapters described herein. In one preferred embodiment, the modified ribonucleotides are 2'-o-methyl ribonucleotides.

The term "target RNA", as used herein, refers to a ribonucleotide sequence that is sought to be detected. The target RNA may be obtained from any source and may comprise any number of different compositional components. For example, the target RNA is isolated from organisms, tissues, cells, or bodily fluids such as blood. For example, the target RNA encompasses non-coding RNA and/or coding RNA. In particular, the target RNA is a microRNA (miRNA) or a miRNA isoform (an isomiR), a transfer RNA (tRNA), a small interfering RNA (siRNA), or other mature small RNA, and may comprise variants, analogs, and mimics.

Further, it will be appreciated that the term "target RNA" may refer to the target molecule itself as well as to surrogates thereof, for example, amplification products (e.g. cDNA derived therefrom) and native sequences. In certain embodiments, the target RNA is a miRNA or miRNA isoform (an isomiR) molecule. In certain embodiments, the target RNA lacks a poly-A tail. In certain embodiments, the target RNA is a mature small RNA molecule, in particular a non-coding small RNA molecule (i.e. having a length of <200 ribonucleotides, e.g. between 10 and <200 ribonucleotides). The target RNA described herein may be derived from any number of sources, including without limitation, humans and animals. These sources may include, but are not limited to, whole blood, a tissue biopsy, lymph, bone marrow, amniotic fluid, hair, skin, semen, biowarfare agents, anal secretions, vaginal secretions, perspiration, saliva, or buccal swabs. However, various environmental samples (for example, agricultural, water, and soil), research samples generally, purified samples generally, cultured cells and lysed cells may also be used as samples. It will be appreciated that target RNAs may be isolated from samples using any of a variety of procedures known in the art, for example, the Applied Biosystems ABI Prism® 6100 Nucleic Acid PrepStation (Life Technologies, Foster City, CA) and the ABI Prism® 6700 Automated Nucleic Acid Workstation (Life Technologies, Foster City, CA), Ambion® mirVana™ RNA isolation kit (Life Technologies, Austin, TX), and the like.

In one embodiment, the target RNA is any single stranded (non-coding or coding) RNA having a 5' phosphate moiety and a 3' hydroxyl moiety. In one preferred embodiment, the target RNA is RNA having a length of <200 ribonucleotides, e.g. between 10 and <200 ribonucleotides. In one more referred embodiment, the target RNA is RNA having a length of between 10 and 100 ribonucleotides. In one even more preferred embodiment, the target RNA is RNA having a length of between 10 and 50 ribonucleotides. Said RNA is particularly a non-coding RNA, specifically a miRNA or a miRNA isoform (an isomiR).

The term "miRNA" (the designation "microRNA" is also possible), as used herein, refers to a single-stranded RNA molecule. The miRNA may be a molecule of 10 to 50 nucleotides in length, e.g. 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, not including optionally labels and/or elongated sequences (e.g. biotin stretches).

The miRNAs regulate gene expression and are encoded by genes from whose DNA they are transcribed but miRNAs are not translated into protein (i.e. miRNAs are non-coding RNAs). The genes encoding miRNAs are longer than the processed mature miRNA molecules. The miRNA is initially transcribed as a longer precursor molecule (>1000 nucleotides long) called a primary miRNA transcript (pri-miRNA). Pri-miRNAs have hairpin structures that are processed by the Drosha enzyme (as part of the microprocessor complex). After Drosha processing, the pri-miRNAs are only 60-100 nucleotides long, and are called precursor miRNAs (pre-miRNAs). At this point, the pre-miRNA is exported to the cytoplasm, where it encounters the Dicer enzyme. Dicer cuts the miRNA in two, resulting in duplexed miRNA strands. Traditionally, only one of these miRNA arms was considered important in gene regulation: the arm that is destined to be loaded into the RNA-induced silencing complex (RISC), and occurs at a higher concentration in the cell. This is often called the "guide" strand and is designated as miR. The other arm is called the "minor miRNA" or "passenger miRNA", and is often designated as miR*. It was thought that passenger miRNAs were completely degraded, but deep sequencing studies have found that some minor miRNAs persist and in fact have a functional role in gene regulation. Due to these developments, the naming convention has shifted. Instead of the miR/miR* name scheme, a miR-5p/miR-3p nomenclature has been adopted. By the new system, the 5' arm of the miRNA is always designated miR-5p and the 3' arm is miR-3p. The present nomenclature is as follows: The prefix "miR" is followed by a dash and a number, the latter often indicating order of naming. For example, hsa-miR-16 was named and likely discovered prior to hsa-miR-342. A capitalized "miR-" refers to the mature forms of the miRNA (e.g. hsa-miR-16-5p and hsa-miR-16-3p), while the uncapitalized "mir-" refers to the pre-miRNA and the pri-miRNA (e.g. hsa-mir-16), and "MIR" refers to the gene that encodes them. However, as this is a recent change, literature will often refer to the original miR/miR* names. After processing, the duplexed miRNA strands are loaded onto an Argonaute (AGO) protein to form a precursor to the RISC. The complex causes the duplex to unwind, and the passenger RNA strand is discarded, leaving behind a mature RISC carrying the mature, single stranded miRNA. The miRNA remains part of the RISC as it silences the expression of its target genes. While this is the canonical pathway for miRNA biogenesis, a variety of others have been discovered. These include Drosha-independent pathways (such as the mirtron pathway, snoRNA-derived pathway, and shRNA-derived pathway) and Dicer-independent pathways (such as one that relies on AGO for cleavage, and another which is dependent on tRNaseZ).

The term "miRBase", as used herein, refers to a well-established repository of validated miRNAs. The miRBase (website: mirbase.org) is a searchable database of published miRNA sequences and annotation. Each entry in the miRBase Sequence database represents a predicted hairpin portion of a miRNA transcript (termed mir in the database), with information on the location and sequence of the mature miRNA sequence (termed miR). Both hairpin and mature sequences are available for searching and browsing, and entries can also be retrieved by name, keyword, references and annotation. All sequence and annotation data are also available for download. In October 2018, miRbase version 22.1 was released. This is the current version.

The term "isomiR" (or "miRNA isoform"), as used herein, refers to a miRNA that varies slightly in sequence, which results from variations in the cleavage site during miRNA biogenesis or by processes which affect the mature miRNA after the biogenesis has occurred, such as oligouridylation. In particular, imprecise cleavage of Drosha and Dicer or the turnover of miRNAs can result in miRNAs that are heterogeneous in length and/or sequence. IsomiRs (miRNA isoforms) can be divided into three main categories: 3' isomiRs (trimmed or addition of one or more nucleotides at the 3' position), 5' isomiRs (trimmed or addition of one or more nucleotides at the 5' position), and polymorphic isomiRs (some nucleotides within the sequence are different from the wild type mature miRNA sequence). It could be envisioned that the increased expression of miRNA variants, or individual isomiRs, lead to the loss or weakening of the function of the corresponding wild-type mature miRNA or result in the regulation of a different transcriptome. Recent studies suggest that isomiRs probably play vital roles in a variety of cancers, tissues, and cell types. The detection of miRNAs as well as isomiRs is, thus, absolutely required to accurately reflect the underlying biological situation and to make the right diagnostic and treatment decisions.

As used herein, the term "adapter" refers to a polynucleotide that can be ligated to the 5' end of a target RNA (i.e. "5' adapter") or to the 3' end of a target RNA (i.e. "3' adapter"). The nucleotides of the 5' adapter and the 3' adapter may be standard or natural (i.e. adenosine, guanosine, cytidine, thymidine, and uridine) as well as non-standard nucleotides. Non-limiting examples of non-standard nucleotides include inosine, xanthosine, isoguanosine, isocytidine, diaminopyrimidine and deoxyuridine. The adapters may comprise modified or derivatized nucleotides. Non-limiting examples of modifications in the ribose or base moieties include the addition, or removal, of acetyl groups, amino groups, carboxyl groups, carboxymethyl groups, hydroxyl groups, methyl groups, phosphoryl groups and thiol groups. In particular, included are 2'-O-methyl and locked nucleic acids (LNA) nucleotides. Suitable examples of derivatized nucleotides include those with covalently attached dyes, such as fluorescent dyes or quenching dyes, or other molecules such as biotin, digoxygenin, or magnetic particles or microspheres. The adapters may also comprise synthetic nucleotide analogs such as morpholinos or peptide nucleic acids (PNA). Phosphodiester bonds or phosphothioate bonds may link the nucleotides or nucleotide analogs of the linkers.

The length of the 5' and 3' adapter can vary depending upon, for example, the desired length of the ligation product and the desired features of the adapter. In general, the 5' adapter or 3' adapter may range from 15 to 60, e.g. 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60, nucleotides in length.

The 5' adapter as described herein comprises a 5' terminal nucleotide sequence comprising 6 to 15, e.g. 6, 7, 8, 9, 10, 11, 12, 13, 14, or 15, (random) deoxynucleotides, wherein said 6 to 15 (random) deoxynucleotides are reverse complementary to a 5'-terminal sequence of a target RNA. In addition, the 3' adapter as described herein comprises a 3' terminal nucleotide sequence comprising 6 to 15, e.g. 6, 7, 8, 9, 10, 11, 12, 13, 14, or 15, (random) deoxynucleotides, wherein said 6 to 15 (random) deoxynucleotides are reverse complementary to a 3'-terminal sequence of a target RNA. The 5' adapter and the 3' adapter can be present as linear polynucleotide, e.g. after denaturation/when denatured. In this form, the 5' adapter and the 3' adapter is single-stranded. This primary structure may be converted into a secondary structure. In particular, the 5' adapter and the 3' adapter is further capable of forming a stem-loop structure. Thus, the 5' adapter and the 3' adapter can also have a stem-loop structure, e.g. after re-naturation/when re-natured.

Generally, the term "stem-loop structure" refers to a pattern that can occur in single-stranded RNA. The structure is also known as a "hairpin" or "hairpin loop". It occurs when two regions of the same strand, usually complementary in nucleotide sequence when read in opposite directions, base-pair to form a double helix that ends in an unpaired loop.

In particular, the 5' adapter and the 3' adapter that is capable of forming a stem-loop structure comprises a 5' positioned first stem sequence and a 3' positioned second stem sequence that are reverse complementary to each other. The first stem sequence and the second stem sequence form the "double-stranded region" or "double-stranded stem" of the stem-loop adaptor.

In one embodiment, the stem is between 5 and 20, e.g. 5, 6, 7, 8, 9, 10, 11, 12, 13, 14, 15, 16, 17, 18, 19 or 20, nucleotides in length. In one preferred embodiment, the stem is between 5 and 10, e.g. 5, 6, 7, 8, 9, or 10, nucleotides in length.

It should be noted that a portion of a primer may be encoded in the stem. As a general matter, in those embodiments in which a portion of a primer is encoded in the stem, the stem may be longer. In those embodiments in which a portion of a primer is not encoded in the stem, the stem may be shorter.

As used herein, the term "loop" refers to the single-stranded region of the stem-loop structure. In particular, the loop is located between the 5' positioned first stem sequence and the 3' positioned second stem sequence. In other words, the loop is located between the two reverse complementary strands of the stem and typically the loop comprises single-stranded nucleotides, although other moieties such as modified DNA or RNA molecules are also possible. In one embodiment, the loop sequence comprises between 10 and 40 nucleotides, e.g. 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. In one preferred embodiment, the loop sequence comprises between 12 and 20 nucleotides, e.g. 12, 13, 14, 15, 16, 17, 18, 19, or 20 nucleotides. The nucleotides of the loop structure are preferably deoxynucleotides but also ribonucleotides are possible.

It should be noted that a portion of a primer may be encoded in the loop. As a general matter, in those embodiments in which a primer is encoded in the loop, the loop may be longer. In those embodiments in which a primer is not encoded in the loop, the loop may be shorter.

In addition, it should be noted that the 5' adapter as described herein comprises a 5'-terminal sequence that is configured such that it forms a single stranded 5' protrusion after formation of the stem-loop structure. Moreover, it should be noted that the 3' adapter as described herein comprises a 3'-terminal sequence that is configured such that it forms a single stranded 3' protrusion after formation of the stem-loop structure.

The adapter, e.g. 5' adapter and/or 3' adapter, may comprise one or more blocking nucleotides. The term "blocking nucleotide", as used herein, refers to a nucleotide comprising a chemical moiety which prevents or minimizes nucleotide addition by a DNA polymerase. For example, by adding a blocking group to the terminal 3'-OH, the nucleotide is no longer able to participate in phosphodiester bond formation catalyzed by the DNA polymerase. Some non-limiting examples include, an alkyl group, non-nucleotide linkers, phosphorothioate, alkane-diol residues, PNA, LNA, nucleotide analogs comprising a 3'-amino group in place of the 3'-OH group, nucleotide analogs comprising a 5'-OH group in place of the 5'-phosphate group, nucleotide derivatives lacking a 3'-OH group, or biotin. These nucleotides are generally not chain extendable. Other examples of non-extendable nucleotides that can be used include nucleotides that have modified ribose moieties. In certain embodiments, ribonucleotides may serve as non-extendable nucleotides because oligonucleotides terminating in ribonucleotides cannot be extended by certain DNA polymerases. The ribose can be modified to include 3'-deoxy derivatives including those in which the 3'-hydroxy is replaced by a functional group other than hydrogen, for example, as an azide group. In certain embodiments, a non-extendible nucleotide comprises a dideoxynucleotide (ddN), for example but not limited to, a dideoxyadenosine (ddA), a dideoxycytosine (ddC), a dideoxyguanosine (ddG), a dideoxythymidine (ddT), or a dideoxyuridine (ddU).

In particular, the adapter, e.g. 5' adapter and/or 3' adapter, may comprise locked nucleic acids (LNAs). The term "locked nucleic acids (LNAs)", as used herein, refers to modified nucleosides, specifically ribonucleotides, in which the 2'-O and 4'-C atoms of the ribose are joined through a methylene bridge. This additional bridge limits the flexibility normally associated with the ring, essentially locking the structure into a rigid conformation. These nucleic acid analogs are also referred to in some circles as "inaccessible ribonucleotides". LNA nucleotides can be mixed with DNA or RNA residues in the polynucleotide, in effect hybridizing with DNA or RNA according to Watson-Crick base-pairing rules. The inflexible nature of these molecules greatly enhances hybridization stability. Further, polynucleotides containing LNAs offer tremendous discriminatory power, allowing these molecules to distinguish between exact match and mismatched complementary target sequences with very little difficulty. In one embodiment, the 5' adapter and/or the 3' adapter comprise(s) locked nucleotides, in particular ribonucleosides. In one preferred embodiment, the 5' positioned first stem sequence and/or the 3' positioned second stem sequence of the 5' adapter is (are) LNA enhanced. In one another preferred embodiment, the 5' positioned first stem sequence and/or the 3' positioned second stem sequence of the 3' adapter is (are) LNA enhanced.

The 3' adapter may comprise a 3' inverted deoxynucleotide. The term "inverted deoxynucleotide", as used herein, refers to a deoxynucleotide creating a 3'-3' linkage and, thus, prevents undesired nucleotide synthesis from the 3' end of the adapter, e.g. during reverse transcriptase (RT) PCR. In addition, the 3' inverted deoxynucleotide protects the sequence from 3' exonuclease cleavage. In one embodiment, the 3' adapter comprises a 3' inverted deoxynucleotide. In one preferred embodiment, the 3' adapter comprises a 3' inverted deoxynucleotide, wherein the deoxynucleotide is inverted dT, dA, dC, or dG.

The 5' adapter may further comprise in the loop a base lacking spacer, specifically at the 5'-end of the loop. The term "base lacking spacer", as used herein, refers to a moiety allowing the termination of the reverse transcription in a subsequent step. In particular, the reaction terminates at the nucleotide preceding the base lacking spacer in the loop region of the 5' adapter, which prevents the reaction from continuing to the end of the 5' adapter and, thus, generating highly structured cDNAs, which may impair subsequent PCR steps. Particularly, the base lacking spacer is a 2'-dideoxyribose spacer. More particularly, the base lacking spacer is a 1'2'-dideoxyribose spacer. In one embodiment, the 5' adapter comprises in the loop a base lacking spacer, preferably at the 5'-end of the loop. In one preferred embodiment, the 5' adapter comprises in the loop a 2'-dideoxyribose spacer, preferably at the 5'-end of the loop.

In one more preferred embodiment, a 5' adapter, wherein the 5' positioned first stem sequence and/or the 3' positioned second stem sequence of the 5' adapter is (are) LNA enhanced and a 3' adapter, wherein the 5' positioned first stem sequence and/or the 3' positioned second stem sequence of the 3' adapter is (are) LNA enhanced are combined/part of a combination.

In one even more preferred embodiment, a 5' adapter, wherein the 5' positioned first stem sequence and/or the 3' positioned second stem sequence of the 5' adapter is (are) LNA enhanced and a 3' adapter, wherein the 5' positioned first stem sequence and/or the 3' positioned second stem sequence of the 3' adapter is (are) LNA enhanced and wherein the the 3' adapter comprises a 3' inverted deoxynucleotide, e.g. inverted dT, dA, dC, or dG, are combined/part of a combination.

Further disclosed herein is a method of ligating adapters to target RNA in a sample. This method requires that the adapters, in particular 5' and 3' adapters, are annealed to target RNA. Before the adapters, in particular 5' and 3' adapters, are annealed to target RNA, the target RNA is denatured. In addition, the adapters, in particular 5' and 3' adapters, are denatured and subsequently renatured.

The term "annealing", as used herein, refers to a process of heating and cooling two single-stranded polynucleotides with complementary sequences. Heat breaks all hydrogen bonds and cooling allows new bonds to form between the sequences. During this process, the adapters, in particular 5' and 3' adapters, attach to the target RNA and form their characteristic stem-loop structure. In particular, the 5' adapter attaches to the 5' end of the target RNA and the 3' adapter attached to the 3' end of the target RNA.

In this respect, it should be noted that the denaturation/renaturation of the adapters, in particular 5' and 3' adapters, takes place separately and in the absence of target RNA in the method of the present invention.

The adapters, in particular 5' and 3' adapters, are then ligated to the target RNA using/with a double stranded RNA ligase, thereby producing a ligation product. As used herein, the term "ligation product" refers to a (DNA/RNA) hybrid molecule comprising at least one adapter and a target RNA. For example, the ligation product may comprise a 5' adapter and a target RNA such as miRNA or isomiR. The ligation product may comprise a 3' adapter and a target RNA such as miRNA or isomiR. In addition, the ligation produced may comprise a 5' adapter, a 3' adapter and a target RNA such as miRNA or isomiR.

In particular, the annealing of the 5' adapter with the target RNA generates a double-stranded (DNA/RNA) hybrid containing a nick of RNA-OH-3'/5'-P-RNA between the 3' end of the adapter and the 5' end of the target RNA. This is an efficient substrate for ligation by a double-stranded RNA ligase. In addition, the annealing of the 3' adapter with the target RNA generates a double-stranded (DNA/RNA) hybrid containing a nick of RNA-OH-3'/5'-P-RNA between the 3' end of the target RNA and the 5' end of the adapter. This is also an efficient substrate for ligation by a double-stranded RNA ligase.

Generally, any double stranded RNA ligase capable of ligating double stranded RNA nicks/RNA structures may be used for this purpose. In one preferred embodiment, the double stranded RNA ligase is a T4 RNA ligase 2 (Rnl2) or a Kod1 ligase. In one more preferred embodiment, the double stranded RNA ligase is a T4 RNA ligase 2 (Rnl2).

The conditions of the ligation reaction are typically adjusted so that the ligase functions near its optimal activity level. A buffering agent may be used to adjust and maintain the pH at the desired level. Representative examples of suitable buffers include, but are not limited to, MOPS, HEPES, TAPS, Bicine, Tricine, TES, PIPES, MES, sodium acetate and Tris buffer.

As used herein, the term "extension reaction" refers to an elongation reaction in which the 3' adapter ligated to the 3' end of the target RNA is extended, in particular in 5' to 3' direction, to form an "extension reaction product" comprising a strand reverse complementary to the target RNA. As used herein, extension reaction is also referred to as "reverse transcription". In some embodiments, the target RNA is a miRNA molecule, and the extension reaction is a reverse transcription reaction comprising a reverse transcriptase, whereby a DNA (in particular cDNA) copy of the ligation product is made. In certain embodiments, the extension reaction is a reverse transcription reaction comprising a polymerase, such as a reverse transcriptase.

The term "reverse transcriptase", as used herein, refers to any enzyme having reverse transcriptase activity. In particular, the term "reverse transcriptase", as used herein, refers to an enzyme used to generate DNA (cDNA) from an RNA template in a process termed reverse transcription. The reverse transcriptase has an RNA-dependent DNA polymerase activity. By means of this activity, a hybrid double strand of RNA and DNA is first built up after presentation of a single-stranded RNA by linking complementary paired DNA building blocks (deoxyribonucleotides). Afterwards, its RNA portion is largely degraded by means of an RNase H activity of a special section of the protein. The remaining DNA single strand is finally completed to the DNA double strand, catalyzed by an additional inherent DNA-dependent DNA polymerase activity of reverse transcriptase. To initiate reverse transcription, the reverse transcriptase requires a primer which serves as a starting point for the reverse transcriptase to synthesize a new strand. This primer is also called RT-primer sequence. The RT-primer depends on the 3' adapter sequence. The RT-primer is reverse complementary to said sequence. In one preferred embodiment, the reverse transcriptase is Maxima H-RT or Tth polymerase. In one more preferred embodiment, the reverse transcriptase is Maxima H-RT.

Described herein is further a method for assaying the ligation product such that the target RNA is detected. In particular, described herein is further a method for assaying the ligation product comprising the cDNA of the target RNA and the 3' adapter such that the target RNA is detected.

The assaying may be quantitative, such that the amount or copies of the target RNA in a sample may be determined. Alternatively, the assaying may be qualitative, such that the presence or absence of a target RNA may be determined in the sample, but its level may not be measured. Thus, the assaying allows the determination and quantification of the target RNA in a sample. Described herein is an amplification method to assay the ligation product. In particular, amplification is carried out using a polymerase chain reaction (PCR). The PCR may be selected from the group consisting of real-time PCR (quantitative PCR or qPCR), preferably Taq-man qPCR, multiplex PCR, nested PCR, high fidelity PR, fast PCR, hot start PCR, and GC-rich PCR. To amplify the ligation product comprising a target RNA, the ligation product is generally converted into a DNA copy.

The terms "amplicon" and "amplification product", as used herein, generally refer to the product of an amplification reaction. An amplicon may be double-stranded or single-stranded, and may include the separated component strands obtained by denaturing a double-stranded amplification product. In certain embodiments, the amplicon of one amplification cycle can serve as a template in a subsequent amplification cycle.

The term "amplifying", as used herein, refers to any means by which at least a part of a target RNA, target RNA surrogate, or combinations thereof, is reproduced, typically in a template-dependent manner, including without limitation, a broad range of techniques for amplifying nucleic acid sequences, either linearly or exponentially. Any of several methods can be used to amplify the target polynucleotide. Any in vitro means for multiplying the copies of a target sequence of nucleic acid can be utilized. These include linear, logarithmic, or other amplification methods. Exemplary methods include polymerase chain reaction (PCR), isothermal procedures (using one or more RNA polymerases, strand displacement, partial destruction of primer molecules, ligase chain reaction (LCR), Q RNA replicase systems, RNA transcription-based systems (e.g., TAS, 3SR), or rolling circle amplification (RCA).

In the context of the present invention, the cDNA of the target RNA is amplified.

The term "Dumbbell PCR (DB-PCR)", as used herein, refers to an efficient and convenient method to distinctively quantify a specific individual small RNA such as a miRNA as well as a specific individual small RNA variant such as an isomiR. In Db-PCR, 5'- and 3' adapters are specifically hybridized and ligated to the 5'- and 3'-ends of target RNAs, respectively, by a double stranded RNA ligase, e.g. T4 RNA ligase 2 (Rnl2). The resultant ligation products with 'dumbbell-like' structures are subsequently quantified, e.g. by TaqMan RT-PCR. The present inventors found that the use of the proprietary 5' and 3' adapters as described herein as well as high specificity of Rnl2 ligation and TaqMan RT-PCR toward target RNAs assured both 5'- and 3'-terminal sequences of target RNAs with single nucleotide resolution so that Db-PCR specifically detected target RNAs but not their corresponding terminal variants. Db-PCR described herein has broad applicability for the quantification of various small RNAs in different cell types. Therefore, Db-PCR provides a much-needed simple method for analyzing RNA terminal heterogeneity.

Residues in two or more polynucleotides are said to "correspond" to each other if the residues occupy an analogous position in the polynucleotide structures. It is well known in the art that analogous positions in two or more polynucleotides can be determined by aligning the polynucleotide sequences based on nucleic acid sequence or structural similarities. Such alignment tools are well known to the person skilled in the art and can be, for example, obtained on the World Wide Web, for example, ClustalW or Align using standard settings, preferably for Align EMBOSS::needle, Matrix: Blosum62, Gap Open 10.0, Gap Extend 0.5.

The term "disease", as used herein, refers to an abnormal condition that affects the body of an individual. A disease is often construed as a medical condition associated with specific symptoms and signs. In humans, the term "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality. The disease may be a disease selected from the group consisting of neurodegenerative disease, an autoimmune disease, an infectious disease, and cancer.

The term "therapeutic treatment/therapy", as used herein, relates to any treatment/therapy which improves the health status and/or prolongs (increases) the lifespan of a patient. Said treatment/therapy may eliminate the disease in a patient, arrest, inhibit, or slow the development of a disease in a patient, decrease the frequency or severity of symptoms in a patient, and/or decrease the recurrence in a patient who currently has or who previously has had a disease.

The term "sample", as used herein, refers to any sample comprising target RNAs, particularly coding and/or non-coding, more particularly small non-coding, target RNAs. Said sample is specifically derived from the body of a patient/subject. Said sample specifically comprises target RNAs, in particular small non-coding target RNA, isolated from organisms, tissues, cells, or bodily fluids such as blood. Thus, the sample is particularly a biological sample.

The term "biological sample", as used herein, refers to any sample having a biological origin and/or comprises biological material. The biological sample may be a body fluid sample, e.g. a blood sample or urine sample, or a tissue sample, e.g. a tissue biopsy sample. Biological samples may be mixed or pooled, e.g. a sample may be a mixture of a blood sample and a urine sample.

The term "body fluid sample", as used herein, refers to any liquid sample comprising target RNA. Said sample is specifically derived from the body of a patient/subject. Said body fluid sample may be a urine sample, blood sample, sputum sample, breast milk sample, cerebrospinal fluid (CSF) sample, cerumen (earwax) sample, gastric juice sample, mucus sample, lymph sample, endolymph fluid sample, perilymph fluid sample, peritoneal fluid sample, pleural fluid sample, saliva sample, sebum (skin oil) sample, semen sample, sweat sample, tears sample, cheek swab, vaginal secretion sample, liquid biopsy, or vomit sample including components or fractions thereof. The term "body fluid sample" also encompasses body fluid fractions, e.g. blood fractions, urine fractions or sputum fractions. Body fluid samples may be mixed or pooled. Thus, a body fluid sample may be a mixture of a blood and a urine sample or a mixture of a blood and cerebrospinal fluid sample.

The term "blood sample", as used herein, encompasses whole blood or a blood fraction. Preferably, the blood fraction is selected from the group consisting of a blood cell fraction, plasma, and serum. In particular the blood fraction is selected from the group consisting of a blood cell fraction and plasma or serum. For example, the blood cell fraction encompasses erythrocytes, leukocytes, and/or thrombocytes.

The whole blood sample may be collected by means of a blood collection tube. It is, for example, collected in a PAXgene Blood RNA tube, in a Tempus Blood RNA tube, in an EDTA-tube, in a Na-citrate tube, Heparin-tube, or in a ACD-tube (Acid citrate dextrose).

The whole blood sample may also be collected by means of a bloodspot technique, e.g. using a Mitra Microsampling Device. This technique requires smaller sample volumes, typically 45-60 µl for humans or less. For example, the whole blood may be extracted from the patient via a finger prick with a needle or lancet. Thus, the whole blood sample may have the form of a blood drop. Said blood drop is then placed on an absorbent probe, e.g. a hydrophilic polymeric material such as cellulose, which is capable of absorbing the whole blood. Once sampling is complete, the blood spot is dried in air before transferring or mailing to labs for processing. Because the blood is dried, it is not considered hazardous. Thus, no special precautions need be taken in handling or shipping. Once at the analysis site, the desired components, e.g. miRNAs, are extracted from the dried blood spots into a supernatant which is then further analyzed.

The term "level", as used herein, refers to an amount (measured for example in grams, mole, or ion counts) or concentration (e.g. absolute or relative concentration, e.g. reads per million (RPM) or NGS counts) of a target RNA. The term "level", as used herein, also comprises scaled, normalized, or scaled and normalized amounts or values. In particular, the level of the target RNA is determined by sequencing, preferably next generation sequencing (e.g. ABI SOLID, Illumina Genome Analyzer, Roche 454 GS FL, BGISEQ), nucleic acid hybridization (e.g. microarray or beads), nucleic acid amplification (e.g. PCR, RT-PCR, qRT-PCR, or high-throughput RT-PCR), polymerase extension, mass spectrometry, flow cytometry (e.g. LUMINEX), or any combination thereof specifically, the level of the target RNA is the expression level of said target RNA.

The term "patient", as used herein, refers to any individual for whom it is desired to know whether she or he suffers from a disease or condition. In particular, the term "patient", as used herein, refers to an individual suspected to be affected by a disease or condition. The patient may be diagnosed to be affected by a disease or condition or may be diagnosed to be not affected by a disease or condition, i.e. healthy. The term "patient", as used herein, also refers to an individual which is affected by a disease or condition. The patient may be retested for the disease or condition and may be diagnosed to be still affected by the disease or condition, or not affected by the disease or condition anymore, i.e. healthy, for example after therapeutic intervention. The patient may be a human or an animal. Human individuals are particularly preferred.

The term "(control) subject", as used herein, refers to a subject known to be affected by a disease or condition or known to be not affected by a disease or condition, i.e. healthy. The (control) subject may be a human or an animal. Human individuals are particularly preferred.

In the context of the present invention, the term "kit of parts (in short: kit)" is understood to be any combination of at least some of the components identified herein, which are combined, coexisting spatially, to a functional unit, and which can contain further components.

Embodiments of the Invention

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous, unless clearly indicated to the contrary.

The present inventors have developed a Dumbbell PCR (DB PCR) based method, which exploits the ability of a double stranded RNA ligase, particularly RNA ligase 2 (Rnl2), to specifically join the nicks in hybridized double stranded RNA molecule. Only correctly hybridized adaptors both to the 5' and the 3' end of the isomiRs enable the formation of the ligated RNA that can be used as template for cDNA synthesis. This method is able to specifically and efficiently determine and quantify the expression of target RNA (e.g. miRNA) as well as of target RNA variants having specific terminal sequences (e.g. isomiR). Second layer of specificity is introduced by a TaqMan probe, that can align to a user-defined region of cDNA sequence. The Dumbbell PCR (DB PCR) based method developed by the present inventors can be used at any hospital/clinical or research center and allows the analysis of clinical samples in a simple, fast, reliable, precise, and cost-effective manner. Due to this method, the specificity and sensitivity of a diagnostic tests can further be improved. A kit suitable for the above purpose is also provided.

Thus, in a first aspect, the present invention relates to a 5' adapter comprising in the following order from 5' to 3'
  (i) a 5' terminal nucleotide sequence comprising 6 to 15, e.g. 6, 7, 8, 9, 10, 11, 12, 13, 14, 15, or 16, deoxynucleotides wherein said 6 to 15 deoxynucleotides are reverse complementary to a 5'-terminal sequence of a target RNA, and
  (ii) a nucleotide sequence capable of forming a stem-loop structure containing a loop and a double stranded stem, wherein at least 2, e.g. 2, 3, or 4, nucleotides at its 3' end are ribonucleotides or modified ribonucleotides and wherein the nucleotide sequence is (preferably) locked nucleotide-(LNA-) enhanced.

Preferably, the LNA enhanced sequence comprises between 2 to 10, e.g. 2, 3, 4, 5, 6, 7, 8, 9, or 10, more preferably 3, locked nucleotides, specifically ribonucleotides.

In particular, the nucleotide sequence of the 5' adapter comprises deoxynucleotides and ribonucleotides.

The 5' adapter may range from 15 to 60, e.g. 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60, nucleotides in length.

The 5' adapter may be present as linear polynucleotide, particularly in single-stranded form, e.g. after denaturation/when denatured. The 5' adapter is a polynucleotide that can be attached/ligated to the 5' end of a target RNA. When attached/ligated to the 5' end of a target RNA, the 5' adapter has a stem-loop structure. The attachment/ligation is possible as the 5' adapter comprises between 6 to 15, e.g. 6, 7, 8, 9, 10, 11, 12, 13, 14, 15, or 16, deoxynucleotides which are reverse complementary to a 5'-terminal sequence of a target RNA. The target RNA is preferably a miRNA or isomiR comprised in/part of miRbase version 22.1.

In one embodiment, the nucleotide sequence capable of forming a stem-loop structure comprises a 5' positioned first stem sequence and a 3' positioned second stem sequence that are reverse complementary to each other. Thus, the 5' positioned first stem sequence and the 3' positioned second stem sequence can form the double stranded stem.

The double stranded stem may have a length of between 5 and 20, e.g. 5, 6, 7, 8, 9, 10, 11, 12, 13, 14, 15, 16, 17, 18, 19 or 20, nucleotides.

Preferably, each one of the 5' positioned first stem sequence and the 3' positioned second stem sequence has a length of between 5 to 10, e.g. 5, 6, 7, 8, 9, or 10, nucleotides. Particularly, the 5' positioned first stem sequence and the 3' positioned second stem sequence have the same length, e.g. a length of 5, 6, 7, 8, 9, or 10 nucleotides.

More preferably, the 5' positioned first stem sequence and/or the 3' positioned second stem sequence is (are) LNA enhanced. Particularly, the LNA enhanced sequence comprises between 2 to 5, e.g. 2, 3, 4, or 5, more particularly 3, locked nucleotides, specifically ribonucleotides.

Examples of locked ribonucleotides are LNA-guanine, LNA-adenosine or LNA-cytosine. Even more preferably, the 5' positioned first stem sequence is LNA enhanced. Particularly, the LNA enhanced sequence comprises between 2 to 5, e.g. 2, 3, 4, or 5, more particularly 3, locked nucleotides, specifically ribonucleotides. Examples of locked ribonucleotides are LNA-guanine, LNA-adenosine or LNA-cytosine. Specifically, every, every second, or every third nucleotide may be LNA enhanced in the 5' positioned first stem sequence and/or the 3' positioned second stem sequence.

Thus, the 5' positioned first stem sequence and/or the 3' positioned second stem sequence may comprise (a mixture of) deoxynucleotides and ribonucleotides (e.g. LNA-enhanced) or the 5' positioned first stem sequence and/or the 3' positioned second stem sequence may comprise ribonucleotides. Said ribonucleotides include ribonucleotides which are LNA-enhanced.

In one further embodiment, the nucleotide sequence capable of forming a stem-loop structure comprises a loop sequence which is located between the 5' positioned first stem sequence and the 3' positioned second stem sequence. The loop sequence may comprise between 10 and 40, e.g. 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, nucleotides. Preferably, the loop sequence comprises between 12 and 20, e.g. 12, 13, 14, 15, 16, 17, 18, 19, or 20, nucleotides, e.g. deoxynucleotides and/or ribonucleotides. More preferably, the loop sequence comprises between 12 and 20, e.g. 12, 13, 14, 15, 16, 17, 18, 19, or 20, deoxynucleotides.

In one preferred embodiment, the nucleotide sequence capable of forming a stem-loop structure containing a loop and a double stranded stem comprises deoxynucleotides with the exception of the at least two nucleotides at its 3' end which are ribonucleotides or modified ribonucleotides, preferably 2'-o-methyl ribonucleotides, and the locked ribonucleotides.

In one another embodiment, the 5'-terminal sequence is configured such that it forms a single stranded 5' protrusion after formation of the stem-loop structure.

In one preferred embodiment, the 6 to 15, e.g. 6, 7, 8, 9, 10, 11, 12, 13, 14, 15, or 16, deoxynucleotides which are reverse complementary to the 5'-terminal sequence of a target RNA encompass G and C but not more than 4, e.g. 1, 2, 3, or 4, in a row.

In one more preferred embodiment, the 5' adapter has the following sequence from 5' to 3':
  (6-15x)NCGTGGCGTGGAGTGTGTGCTTTGCCA-rCrG (SEQ ID NO: 1), wherein "r" stands for ribonucleotide, wherein "(6-15x)N" designates the sequence reverse complementary to a 5' terminal sequence of a target RNA, and wherein one or more nucleotides in the underlined portion and/or one or more nucleotides in the double underlined portion are LNA enhanced, or is a variant of this sequence.

For example, every, every second, or every third nucleotide may be LNA enhanced in the underlined portion and/or in the double underlined portion specified above.

In one even more preferred embodiment, the 5' adapter has the following sequence from 5' to 3':

(6-15×)NCGTGGCGTGGAGTGTGTGCTTTGCCA-rCrG (SEQ ID NO: 1), wherein "r" stands for ribonucleotide, wherein "(6-15×)N" designates the sequence reverse complementary to a 5' terminal sequence of a target RNA, and wherein one or more (e.g. 1, 2, or 3) of the nucleotides in bold letters are LNA enhanced, or is a variant of this sequence.

Specifically, the LNA enhanced nucleotides are ribonucleotides.

The 5' adapter variant as described above has a sequence having at least 80%, preferably 85%, more preferably 90%, even more preferably 95%, and still even more preferably 99%, e.g. 80, 81, 82, 83, 84, 85, 86, 87, 88, 89, 90, 91, 92, 93, 94, 95, 96, 97, 98, or 99%, sequence identity to the sequence according to SEQ ID NO: 1. Such a 5' adapter variant still comprises the at least 2 nucleotides at its 3' end which are ribonucleotides or modified ribonucleotides. In addition, such a 5' adapter variant is still LNA enhanced. Moreover, such a 5' adapter variant is still capable of forming a stem-loop structure containing a loop and a double stranded stem. The skilled person can readily assess whether a 5' adapter variant is still capable of forming a stem-loop structure containing a loop and a double stranded stem. For example, the experimental section provides sufficient information in this respect.

In one particular embodiment, the 5' adapter as described above comprises a base-lacking spacer (e.g. a base-lacking 1', 2'-dideoxyribose spacer) in the loop region. A 5' adapter having a base-lacking spacer in the loop region has preferably the following sequence from 5' to 3':

(6-15×)NCGTGGCG/idSp/TGGAGTGTGTGCTTTGC-CArCrG (SEQ ID NO: 29), wherein "r" stands for ribonucleotide, wherein "(6-15×)N" designates the sequence reverse complementary to a 5' terminal sequence of a target RNA, wherein "idSp" stands for base lacking spacer, and wherein one or more nucleotides in the underlined portion and/or one or more nucleotides in the double underlined portion are LNA enhanced, or is a variant of this sequence.

Specifically, the LNA enhanced nucleotides are ribonucleotides.

In one more particular embodiment, the 5' adapter comprising a base-lacking spacer (e.g. a base-lacking 1', 2'-dideoxyribose spacer) in the loop region has the following sequence from 5' to 3': (6-15×)NCGTGGCG/idSp/TGGAGTGTGTGCTTTGCCArCrG (SEQ ID NO: 29), wherein "r" stands for ribonucleotide, wherein "(6-15×)N" designates the sequence reverse complementary to a 5' terminal sequence of a target RNA, wherein "idSp" stands for base lacking spacer, and wherein one or more (e.g. 1, 2, or 3) of the nucleotides in bold letters are LNA enhanced, or is a variant of this sequence.

The 5' adapter variant as described above has a sequence having at least 80%, preferably 85%, more preferably 90%, even more preferably 95%, and still even more preferably 99%, e.g. 80, 81, 82, 83, 84, 85, 86, 87, 88, 89, 90, 91, 92, 93, 94, 95, 96, 97, 98, or 99%, sequence identity to the sequence according to SEQ ID NO: 29. Such a 5' adapter variant still comprises the at least 2 nucleotides at its 3' end which are ribonucleotides or modified ribonucleotides. Further, such a 5' adapter variant is still LNA enhanced. Furthermore, such a 5' adapter still comprises a base lacking spacer. In addition, such a 5' adapter variant is still capable of forming a stem-loop structure containing a loop and a double stranded stem. The skilled person can readily assess whether a 5' adapter variant is still capable of forming a stem-loop structure containing a loop and a double stranded stem. For example, the experimental section provides sufficient information in this respect.

In one another particular embodiment, the 5' adapter as described above does not comprise a base-lacking spacer (e.g. a base-lacking 1', 2'-dideoxyribose spacer) in the loop region.

The 5' adapter as described above can bind to any RNA target (specifically to the 5' end of any RNA target) just by exchanging the variable protrusions. In particular, the 6 to 15, e.g. 6, 7, 8, 9, 10, 11, 12, 13, 14, 15, or 16, deoxynucleotides in the 5' terminal nucleotide sequence of the 5' adapter have only to be selected in a way that they are reverse complementary to the target RNA (specifically to the 5' end of the target RNA) to be detected. The 5' adapter is especially used jointly with the 3' adapter.

The 5' adapter as described above may be present in denatured or renatured form.

In one another embodiment, the target RNA is any single stranded RNA having a 5' phosphate moiety and a 3' hydroxyl moiety. Particularly, the target RNA is RNA having a length of <200 ribonucleotides, e.g. between 10 and <200 ribonucleotides. More particularly, the target RNA is RNA having a length of between 10 and 100 ribonucleotides. Even more particularly, the target RNA is RNA having a length of between 10 and 50 ribonucleotides. Said RNA is specifically a miRNA or a miRNA isoform (an isomiR).

In a second aspect, the present invention relates to a 3' adapter comprising in the following order from 5' to 3'
 (i) a nucleotide sequence capable of forming a stem-loop structure containing a loop and a double stranded stem, wherein the 5'-terminal nucleotide is phosphorylated and wherein the nucleotide sequence is (preferably) locked nucleotide-(LNA-) enhanced, and
 (ii) a 3' terminal nucleotide sequence comprising 6 to 15, e.g. 6, 7, 8, 9, 10, 11, 12, 13, 14, 15, or 16, deoxynucleotides, wherein said 6 to 15 deoxynucleotides are reverse complementary to a 3'-terminal sequence of a target RNA and wherein the 3' terminal deoxynucleotide is an inverted deoxynucleotide.

Preferably, the LNA enhanced sequence comprises between 2 to 10, e.g. 2, 3, 4, 5, 6, 7, 8, 9, or 10, more preferably 3, locked nucleotides, specifically ribonucleotides.

In particular, the nucleotide sequence of the 3' adapter comprises deoxynucleotides and ribonucleotides.

The 3' adapter may range from about 15 to about 60, e.g. 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60, nucleotides in length.

The 3' adapter may be present as linear polynucleotide, particularly in single-stranded form, e.g. after denaturation/when denatured. The 3' adapter is a polynucleotide that can be attached/ligated to the 3' end of a target RNA. When attached/ligated to the 3' end of a target RNA, the 3' adapter has a stem-loop structure. The attachment/ligation is possible as the 3' adapter comprises between 6 to 15, e.g. 6, 7, 8, 9, 10, 11, 12, 13, 14, 15, or 16, deoxynucleotides which are reverse complementary to a 3'-terminal sequence of a target RNA. The target RNA is preferably a miRNA or isomiR comprised in miRbase version 22.1.

In one embodiment, the nucleotide sequence capable of forming a stem-loop structure comprises a 5' positioned first stem sequence and a 3' positioned second stem sequence that are reverse complementary to each other. Thus, the 5' positioned first stem sequence and the 3' positioned second stem sequence can form the double stranded stem.

The double stranded stem may have a length of between 5 and 20, e.g. 5, 6, 7, 8, 9, 10, 11, 12, 13, 14, 15, 16, 17, 18, 19 or 20, nucleotides.

Preferably, each one of the 5' positioned first stem sequence and the 3' positioned second stem sequence has a length of between 5 to 10, e.g. 5, 6, 7, 8, 9, or 10, nucleotides. Particularly, the 5' positioned first stem sequence and the 3' positioned second stem sequence have the same length, e.g. a length of 5, 6, 7, 8, 9, or 10 nucleotides.

More preferably, the 5' positioned first stem sequence and/or the 3' positioned second stem sequence is (are) LNA enhanced. Particularly, the LNA enhanced sequence comprises between 2 to 5, e.g. 2, 3, 4, or 5, more particularly 3, locked nucleotides, specifically ribonucleotides.

Examples of locked ribonucleotides are LNA-guanine, LNA-adenosine or LNA-cytosine. Even more preferably, the 3' positioned second stem sequence is LNA enhanced. Particularly, the LNA enhanced sequence comprises between 2 to 5, e.g. 2, 3, 4, or 5, more particularly 3, locked nucleotides, specifically ribonucleotides. Examples of locked ribonucleotides are LNA-guanine, LNA-adenosine or LNA-cytosine. Specifically, every, every second, or every third nucleotide may be LNA enhanced in the 5' positioned first stem sequence and/or the 3' positioned second stem sequence.

Thus, the 5' positioned first stem sequence and/or the 3' positioned second stem sequence may comprise (a mixture of) deoxynucleotides and ribonucleotides (e.g. LNA-enhanced) or the 5' positioned first stem sequence and/or the 3' positioned second stem sequence may comprise ribonucleotides. Said ribonucleotides include ribonucleotides which are LNA-enhanced.

In one further embodiment, the nucleotide sequence capable of forming a stem-loop structure comprises a loop sequence which is located between the 5' positioned first stem sequence and the 3' positioned second stem sequence. The loop sequence may comprise between 10 and 40, e.g. 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, nucleotides. Preferably, the loop sequence comprises between 12 and 20, e.g. 12, 13, 14, 15, 16, 17, 18, 19, or 20 nucleotides, e.g. deoxynucleotides and/or ribonucleotides. More preferably, the loop sequence comprises between 12 and 20, e.g. 12, 13, 14, 15, 16, 17, 18, 19, or 20, deoxynucleotides.

In one another embodiment, the 3'-terminal sequence is configured such that it forms a single stranded 3' protrusion after formation of the stem-loop structure.

In one preferred embodiment, the 6 to 15, e.g. 6, 7, 8, 9, 10, 11, 12, 13, 14, 15, or 16, deoxynucleotides which are reverse complementary to the 3'-terminal sequence of a target RNA encompass G and C but not more than 4, e.g. 1, 2, 3, or 4, in a row.

In one another preferred embodiment, the inverted deoxynucleotide is inverted dT, dA, dC, or dG. In this respect, it should be noted that the 3' inverted deoxynucleotide creates a 3'-3' linkage and, thus, prevents undesired nucleotide synthesis from the 3' end of the adapter, e.g. during RT-PCR. In addition, the 3' inverted deoxynucleotide protects the sequence from 3' exonuclease cleavage.

In one more preferred embodiment, the 3' adapter has the following sequence from 5' to 3': /5Phos/ CTCAGTGCAGGGTCCGAGGTATTCGCACTGAG(6-15x)N/3InvdT/(SEQ ID NO: 2), wherein "/5Phos/" indicates that the 5'-terminal nucleotide is phosphorylated, wherein one or more nucleotides in the underlined portion and/or one or more nucleotides in the double underlined portion are LNA enhanced, wherein "(6-15x)N" designates the sequence reverse complementary to a 3' terminal sequence of a target RNA, and wherein "/3InvdT/" stands for 3' inverted deoxynucleotide, or
is a variant of this sequence For example, every, every second, or every third nucleotide may be LNA enhanced in the underlined portion and/or in the double underlined portion specified above.

In one even more preferred embodiment, the 3' adapter has the following sequence from 5' to 3': /5Phos/ CTCAGTGCAGGGTCCGAGGTATTCGCACTGAG(6-15x)N/3InvdT/(SEQ ID NO: 2), wherein "/5Phos/" indicates that the 5'-terminal nucleotide is phosphorylated, wherein one or more (e.g. 1, 2, or 3) of the nucleotides in bold letters are LNA enhanced, wherein "(6-15x)N" designates the sequence reverse complementary to a 3' terminal sequence of a target RNA, and wherein "/3InvdT/" stands for 3' inverted deoxynucleotide, or is a variant of this sequence.

Specifically, the LNA enhanced nucleotides are ribonucleotides.

The 3' adapter variant as described above has a sequence having at least 80%, preferably 85%, more preferably 90%, even more preferably 95%, still even more preferably 99%, e.g. 80, 81, 82, 83, 84, 85, 86, 87, 88, 89, 90, 91, 92, 93, 94, 95, 96, 97, 98, or 99%, sequence identity to the sequence according to SEQ ID NO: 2. Such a 3' adapter variant is still LNA enhanced. Further, the 5'-terminal nucleotide is still phosphorylated in such a 3' adapter variant. Furthermore, the 3' terminal deoxynucleotide is still an inverted deoxynucleotide in such a 3' adapter variant. Moreover, such a 3' adapter variant is still capable of forming a stem-loop structure containing a loop and a double stranded stem. The skilled person can readily assess whether a 3' adapter variant is still capable of forming a stem-loop structure containing a loop and a double stranded stem. For example, the experimental section provides sufficient information in this respect.

The 3' adapter as described above can bind to any RNA target (specifically to the 3' end of any RNA target) just by exchanging the variable protrusions. In particular, the 6 to 15, e.g. 6, 7, 8, 9, 10, 11, 12, 13, 14, 15, or 16, deoxynucleotides in the 3' terminal nucleotide sequence of the 3' adapter have only to be selected in a way that they are reverse complementary to the target RNA (specifically to the 3' end of the target RNA) to be detected. The 3' adapter is especially used jointly with the 5' adapter.

The 3' adapter as described above may be present in denatured or renatured form.

In one another embodiment, the target RNA is any single stranded RNA having a 5' phosphate moiety and a 3' hydroxyl moiety. Particularly, the target RNA is RNA having a length of <200 ribonucleotides, e.g. between 10 and <200 ribonucleotides. More particularly, the target RNA is RNA having a length of between 10 and 100 ribonucleotides. Even more particularly, the target RNA is RNA having a length of between 10 and 50 ribonucleotides. Said RNA is specifically a miRNA or a miRNA isoform (an isomiR).

In a third aspect, the present invention relates to a combination comprising
the 5' adapter according to the first aspect, and
the 3' adapter according to the second aspect.

The 5' adapter according to the first aspect and the 3' adapter according to the second aspect may be present in the combination individually or together. For example, the 5' adapter according to the first aspect may be comprised in a (first) composition and the 3' adapter according to the second aspect may be comprised in another/different (second) composition. Alternatively, the 5' adapter according to the first aspect and the 3' adapter according to the second aspect may be comprised in a single composition. The composition may be an aqueous solution such as water or a buffer solution.

In one preferred embodiment, the total length of the 5' terminal nucleotide sequence comprising 6 to 15 deoxynucleotides, e.g. 6, 7, 8, 9, 10, 11, 12, 13, 14, or 15, and the 3' terminal nucleotide sequence comprising 6 to 15 deoxynucleotides, e.g. 6, 7, 8, 9, 10, 11, 12, 13, 14, or 15, is shorter by at least 2, e.g. 2, 3, 4, 5, or 6, nucleotides than the length of the target RNA.

In one preferred embodiment,
the 5' adapter
having the following sequence from 5' to 3':
(6-15×)NCGTGGCGTGGAGTGTGTGCTTTGCCA-rCrG (SEQ ID NO: 1), wherein "r" stands for ribonucleotide, wherein "(6-15×)N" designates the sequence reverse complementary to a 5' terminal sequence of a target RNA, and wherein one or more nucleotides in the underlined portion and/or one or more nucleotides in the double underlined portion are LNA enhanced, or a variant of this sequence, and
the 3' adapter
having the following sequence from 5' to 3':
/5Phos/CTCAGTGCAGGGTCCGAGGTATTCGCACT-GAG(6-15×)N/3InvdT/(SEQ ID NO: 2), wherein "/5Phos/" indicates that the 5'-terminal nucleotide is phosphorylated, wherein one or more nucleotides in the underlined portion and/or one or more nucleotides in the double underlined portion are LNA enhanced, wherein "(6-15×)N" designates the sequence reverse complementary to a 3' terminal sequence of a target RNA, and wherein "/3InvdT/" stands for 3' inverted deoxynucleotide, or a variant of this sequence are combined/part of the combination.

Specifically, the LNA enhanced nucleotides are ribonucleotides.

In one more preferred embodiment,
the 5' adapter
having the following sequence from 5' to 3':
(6-15×)NCGTGGCGTGGAGTGTGTGCTTTGCCA-rCrG (SEQ ID NO: 1), wherein "r" stands for ribonucleotide, wherein "(6-15×)N" designates the sequence reverse complementary to a 5' terminal sequence of a target RNA, and wherein one or more (e.g. 1, 2, or 3) of the nucleotides in bold letters are LNA enhanced, or a variant of this sequence, and
the 3' adapter
having the following sequence from 5' to 3':
/5Phos/CTCAGTGCAGGGTCCGAGGTATTCGCACT-GAG(6-15×)N/3InvdT/(SEQ ID NO: 2), wherein "/5Phos/" indicates that the 5'-terminal nucleotide is phosphorylated, wherein one or more (e.g. 1, 2, or 3) of the nucleotides in bold letters are LNA enhanced, wherein "(6-15×)N" designates the sequence reverse complementary to a 3' terminal sequence of a target RNA, and wherein "/3InvdT/" stands for 3' inverted deoxynucleotide, or a variant of this sequence are combined/part of the combination.

Specifically, the LNA enhanced nucleotides are ribonucleotides.

In one particular embodiment,
the 5' adapter
having the following sequence from 5' to 3':
(6-15×)NCGTGGCG/idSp/TGGAGTGTGTGCTTTGC-CArCrG (SEQ ID NO: 29), wherein "r" stands for ribonucleotide, wherein "(6-15×)N" designates the sequence reverse complementary to a 5' terminal sequence of a target RNA, wherein "idSp" stands for base lacking spacer, and wherein one or more nucleotides in the underlined portion and/or one or more nucleotides in the double underlined portion are LNA enhanced, or a variant of this sequence, and
the 3' adapter
having the following sequence from 5' to 3':
/5Phos/CTCAGTGCAGGGTCCGAGGTATTCGCACT-GAG(6-15×)N/3InvdT/(SEQ ID NO: 2), wherein "/5Phos/" indicates that the 5'-terminal nucleotide is phosphorylated, wherein one or more nucleotides in the underlined portion and/or one or more nucleotides in the double underlined portion are LNA enhanced, wherein "(6-15×)N" designates the sequence reverse complementary to a 3' terminal sequence of a target RNA, and wherein "/3InvdT/" stands for 3' inverted deoxynucleotide, or a variant of this sequence are combined/part of the combination.

In one more particular embodiment,
the 5' adapter
having the following sequence from 5' to 3':
(6-15×)NCGTGGCG/idSp/TGGAGTGTGTGCTTTGC-CArCrG (SEQ ID NO: 29), wherein "r" stands for ribonucleotide, wherein "(6-15×)N" designates the sequence reverse complementary to a 5' terminal sequence of a target RNA, wherein "idSp" stands for base lacking spacer, and wherein one or more (e.g. 1, 2, or 3) of the nucleotides in bold letters are LNA enhanced, or a variant of this sequence, and
the 3' adapter
having the following sequence from 5' to 3':
/5Phos/CTCAGTGCAGGGTCCGAGGTATTCGCACT-GAG(6-15×)N/3InvdT/(SEQ ID NO: 2), wherein "/5Phos/" indicates that the 5'-terminal nucleotide is phosphorylated, wherein one or more (e.g. 1, 2, or 3) of the nucleotides in bold letters are LNA enhanced, wherein "(6-15×)N" designates the sequence reverse complementary to a 3' terminal sequence of a target RNA, and wherein "/3InvdT/" stands for 3' inverted deoxynucleotide, or a variant of this sequence are combined/part of the combination.

Specifically, the LNA enhanced nucleotides are ribonucleotides.

In a fourth aspect, the present invention relates to a method of ligating two adapters to a target RNA in a sample comprising the steps of:
(i) providing a composition comprising a denatured target RNA in a sample, the renatured 5' adapter according to the first aspect, and the renatured 3' adapter according to the second aspect, wherein the 5' adapter and the 3' adapter are annealed to the target RNA, and
(ii) ligating the 5' adapter and the 3' adapter to the target RNA using/with a double stranded RNA ligase, thereby producing a ligation product.

The annealing of the adapters, in particular 5' and 3' adapters, to the target RNA requires that the target RNA is present in denatured form. In one embodiment, the denatured target RNA is produced by heating the target RNA at between 65° C. and 75° C., e.g. 65, 66, 67, 68, 69, 70, 71, 72, 73, 74, or 75° C., preferably at 70° C., for between 1 to 3 minutes, e.g. 1, 2, or 3, minutes, preferably for 2 minutes.

For example, the denatured target RNA is produced by heating the target RNA at 70° C. for 2 minutes.

It is preferred that the target RNA is immediately placed on ice after denaturation.

For the denaturation step, the target RNA is preferably given to an aqueous solution, e.g. water, or to a buffer solution.

As to the adapters, in particular 5' and 3' adapters, a denaturation and a renaturation step is required so that they can from a stem-loop structure which allows annealing to the target RNA. Annealing is a process of heating and cooling adapters with complementary sequences. Heat breaks all hydrogen bonds and cooling allows new bonds to form between the sequences. During this process, the adapters, in particular 5' and 3' adapters, attach to the denatured target RNA and form their characteristic stem-loop structure. In particular, the 5' adapter attaches to the 5' end of the target RNA and the 3' adapter attaches to the 3' end of the target RNA. It is preferred that the adapters, in particular 5' and 3' adapters, are denatured and renatured together, i.e. in a common reaction vessel. It is further preferred that the denaturation/renaturation of the adapters, in particular 5' and 3' adapters, takes place separately and in the absence of target RNA.

In one embodiment, the renatured 5' adapter is produced by
  denaturing the 5' adapter at between 75° C. and 85° C., e.g. 75, 76, 77, 78, 79, 80, 81, 82, 83, 84, or 85° C., preferably at 82° C., for between 1 to 3 minutes, e.g. 1, 2, or 3 minutes, preferably for 2 minutes, and
  renaturing the 5' adapter by cooling down to 4° C., preferably at a rate of 0.1° C./s.

For example, the renatured 5' adapter is produced by denaturing the 5' adapter at 82° C. for 2 minutes and by renaturing the 5' adapter by cooling down to 4° C., preferably at a rate of 0.1° C./s.

In one additional or alternative embodiment, the renatured 3' adapter is produced by
  denaturing the 3' adapter at between 75° C. and 85° C., e.g. 75, 76, 77, 78, 79, 80, 81, 82, 83, 84, or 85° C., preferably at 82° C., for between 1 to 3 minutes, e.g. 1, 2, or 3 minutes, preferably for 2 minutes, and
  renaturing the 3' adapter by cooling down to 4° C., preferably at a rate of 0.1° C./s.

For example, the renatured 3' adapter is produced by denaturing the 3' adapter at 82° C. for 2 minutes, and by renaturing the 3' adapter by cooling down to 4° C., preferably at a rate of 0.1° C./s. For the denaturation and renaturation step, the adapters, in particular 5' and 3' adapters, are preferably given to an aqueous buffer comprising 10 mM TRIS HCl pH 7.5, 50 mM NaCl, and 0.1 mM EDTA. In other words, the denaturing and renaturing of the adapters, in particular 5' and 3' adapters, is preferably carried out in an aqueous buffer comprising 10 mM TRIS HCl pH 7.5, 50 mM NaCl, and 0.1 mM EDTA.

The composition provided in step (i) of the above method is specifically produced by mixing the denatured target RNA, the renatured 5' adapter according to the first aspect, and the renatured 3' adapter according to the second aspect with each other, thereby annealing the 5' adapter and the 3' adapter to the target RNA. Thus, the adapters, in particular 5' and 3' adapters, are annealed/ligated to the target RNA at the same time. In addition, the denatured target RNA is only mixed with the adapters, in particular 5' and 3' adapters, before the annealing/ligation reaction. In other words, the adapters, in particular 5' and 3' adapters, are only mixed with the target RNA before the annealing/ligation reaction. This has the advantage that stable adapter structure is formed in the absence of RNA which could interfere with this process through abundant RNAs, such as ribosomal RNAs.

The annealing of the 5' adapter with the target RNA particularly generates a double-stranded (DNA/RNA) hybrid containing a nick of RNA-OH-3'/5'-P-RNA between the 3' end of the adapter and the 5' end of the target RNA. This is an efficient substrate for ligation by a double stranded RNA ligase.

In addition, the annealing of the 3' adapter with the target RNA particularly generates a double-stranded (DNA/RNA) hybrid containing a nick of RNA-OH-3'/5'-P-RNA between the 3' end of the target RNA and the 5' end of the adapter. This is a substrate for ligation by a double stranded RNA ligase.

The ligation is usually carried out in a ligation buffer. An exemplarily ligation buffers is described in the experimental section of the present patent application. In one preferred embodiment, the ligation buffer comprises polyethylene glycol (PEG), e.g. PEG 8000 (5%), and/or adenosine triphosphate (ATP), e.g. 1 mM ATP. The present inventors have noted that PEG had the effect on the ligation reaction such that it functions as molecular crowding agent and/or ATP had the effect on the ligation reaction such that increased concentrations facilitate the ligation reactions.

In one embodiment, the ligation is carried out
  between 36° C. and 38° C., e.g. 36, 37, or 38° C., preferably at 37° C., for between 30 minutes and 1.5 hours, e.g. 30, 35, 40, 45, 50, 55 minutes, 1, 1.25, or 1.5 hour(s), preferably for 1 hour, or between 15° C. and 20° C., e.g. 15, 16, 17, 18, 19, or 20° C., preferably at 16° C., for between 30 minutes and 2 hours, e.g. 30, 35, 40, 45, 50, 55 minutes, 1, 1.25, 1.5, 1.75, or 2 hour(s), preferably for 1 or 2 hour(s) and then overnight at 12° C. Overnight may mean a time period between 8 and 12 hours, e.g. 8, 9, 10, 11, or 12 hours.

For example, the ligation is carried out
  at 37° C. for 1 hour, or
  at 16° C. for 1 or 2 hour(s) and then overnight at 12° C. Overnight may mean a time period between 8 and 12 hours, e.g. 8, 9, 10, 11, or 12 hours.

The double stranded RNA ligase can be any ligase capable of ligating double stranded RNA nicks/RNA structures. Preferably, the double stranded RNA ligase is a T4 RNA ligase 2 (Rnl2) or a Kod1 ligase.

In this respect, it should be noted that only a perfectly hybridized molecule provides a substrate for the double stranded RNA ligase, in particular Rnl2. Also, in case of protrusion of either strand or a gap that is 2 nucleotides or longer, the Rnl2 will ligate the molecule with much lower efficiency. The adapters, in particular 5' and 3' adapters, described herein provide a dsRNA context with a 6 to 15 nucleotide protrusion that hybridizes to the target RNA. Finally, a 5' phosphate moiety on the target RNA molecule is also required for efficient ligation by Rnl2.

By ligating the adapters, in particular 5' and 3' adapters, to the target RNA using/with a double stranded RNA ligase, a ligation product is produced. The ligation product can be described as a (DNA/RNA) hybrid molecule comprising at least one adapter and a target RNA. For example, the ligation product may comprise a 5' adapter and a target RNA such as miRNA or isomiR. The ligation product may comprise a 3' adapter and a target RNA such as miRNA or isomiR. In addition, the ligation produced may comprise a 5' adapter, a 3' adapter and a target RNA such as miRNA or isomiR.

In a fifth aspect, the present invention relates to a method of determining and/or quantifying a target RNA in a sample comprising the steps of:
(i) carrying out the method according to the fourth aspect,
(ii) reverse transcribing the ligation product, thereby obtaining a cDNA product from the target RNA, and
(iii) amplifying the cDNA, thereby determining and/or quantifying the target RNA.

In one embodiment, the reverse transcription of the ligation product is carried out by
(iia) annealing a primer for reverse transcription (RT-primer) with the ligation product, and
(iib) reverse transcribing the ligation product by using a reverse transcriptase (RT).

In one preferred embodiment, said annealing of a primer for reverse transcription (RT-primer) with the ligation product in step (iia) is carried out at between 60° C. and 80° C., e.g. 60, 61, 62, 63, 64, 65, 66, 67, 68, 69, 70, 71, 72, 73, 74, 75, 76, 77, 78, 79, or 80° C., preferably at 65° C. or 75° C., for between 2 and 7 minutes, e.g. 2, 3, 4, 5, 6, or 7 minutes, preferably 3 or 5 minutes.

For example, said annealing is carried out at 65° C. for between 2 and 7 minutes, e.g. 2, 3, 4, 5, 6, or 7 minutes, preferably 5 minutes. Alternatively, said annealing is carried out at 75° C. for between 2 and 7 minutes, e.g. 2, 3, 4, 5, 6, or 7 minutes, preferably 3 minutes.

In one (additional or alternative) preferred embodiment, said reverse transcribing of the ligation product by using a reverse transcriptase (RT) in step (iib) is carried out
at between 40° C. and 65° C., e.g. 40, 41, 42, 43, 44, 45, 46, 47, 48, 49, 50, 51, 52, 53, 54, 55, 56, 57, 58, 59, 60, 61, 62, 63, 64, or 65° C., preferably at 50° C., 55° C., 58° C., or 62° C., for between 10 and 40 minutes, e.g. 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 minutes, preferably 15 or 30 minutes, and subsequently at between 75° C. and 90° C., e.g. 75, 76, 77, 78, 79, 80, 81, 82, 83, 84, 85, 86, 87, 88, 89, or 90° C., preferably at 85° C., for between 2 and 4 minutes, e.g. 2, 3, or 4 minutes, preferably 3 minutes, or
at between 60° C. and 75° C., e.g. 60, 61, 62, 63, 64, 65, 66, 67, 68, 69, 70, 71, 72, 73, 74, or 75° C., preferably at 68° C., for between 10 and 30 minutes, e.g. 10, 11, 12, 13, 14, 15, 16, 17, 18, 19, 20, 21, 22, 23, 24, 25, 26, 27, 28, 29, or 30 minutes, preferably 15 minutes.

In particular, the reverse transcriptase (RT) is Maxima H-RT or Tth polymerase.

For example, in case the reverse transcriptase (RT) is Maxima H-RT, said reverse transcribing is carried out at 55° C. for 30 minutes and subsequently at 85° C. for 3 minutes.

Alternatively, said reverse transcribing is carried at 50° C., 58° C., or 62° C. for 15 minutes and subsequently at 85° C. for 3 minutes.

For example, in case the reverse transcriptase (RT) is Tth polymerase, said reverse transcribing is carried out at 68° C. for 15 minutes.

In the reverse transcription reaction, the 3' adapter ligated to the 3' end of the target RNA is extended, in particular in 5' to 3' direction, to form a strand reverse complementary to the target RNA. In particular, a cDNA copy of the ligation product is produced in the reverse transcription reaction. For this process, the reverse transcriptase (RT) requires a RT primer. The RT-primer is particularly reverse complementary to the nucleotide sequence capable of forming a stem-loop structure containing a loop and a double stranded stem of the 3' adapter. Thus, the RT-primer sequence depends on the 3' adapter sequence.

In one particular embodiment, the RT-primer has the following sequence from 5' to 3': CTCAGTGCGAATACCTCGGACCCT (SEQ ID NO: 3) or is a variant of this sequence. The RT-primer is, thus, reverse complementary to at least a part of the 3' adapter sequence as described above. In particular, the RT-primer is reverse complementary to nucleotides in the 3' positioned second stem sequence and in the loop sequence. As mentioned above, the 3' adapter sequence is preferably the following from 5' to 3': /5Phos/CTCAGTGCAGGGTCCGAGGTAT-TCGCACTGAG(6-15×)N/3InvdT/(SEQ ID NO: 2), wherein "/5Phos/" indicates that the 5'-terminal nucleotide is phosphorylated, wherein one or more nucleotides in the underlined portion and/or one or more nucleotides in the double underlined portion are LNA enhanced, wherein (6-15×)N designates the sequence reverse complementary to a 3' terminal sequence of a target RNA, and wherein "/3InvdT/" stands for 3' inverted deoxynucleotide. Specifically, the LNA enhanced nucleotides are ribonucleotides.

The RT-primer variant has a sequence having at least 80%, preferably 85%, more preferably 90%, even more preferably 95%, still even more preferably 99%, e.g. 80, 81, 82, 83, 84, 85, 86, 87, 88, 89, 90, 91, 92, 93, 94, 95, 96, 97, 98, or 99%, sequence identity to the sequence according to SEQ ID NO: 3. Such a RT-primer variant is still capable of binding the 3' adapter sequence and allowing reverse transcription which is performed by a reverse transcriptase (RT), e.g. Maxima H-RT or Tth polymerase. The skilled person can readily assess whether a RT primer variant is still capable of binding the 3' adapter sequence and allowing reverse transcription. For example, the experimental section provides sufficient information in this respect.

For assaying the target RNA, its cDNA has to be amplified (see step (iii) of the above method). The assaying may be quantitative, such that the amount or copies of the target RNA in a sample may be determined. Alternatively, the assaying may be qualitative, such that the presence of a target RNA may be determined in the sample, but its level may not be measured. Thus, the assaying allows the determination and quantification of the target RNA in a sample.

In one further (additional or alternative) preferred embodiment, the method further comprises between steps (ii) and (iii) a step of cDNA preamplification. The preamplification reaction is a "simple" PCR reaction and is usually done in a "simple" PCR machine, where, for example, no fluorescent signals are detected and a TaqMan probe is not used. Typically low cycle number is used.

The preamplification requires a DNA polymerase, e.g. a Taq polymerase. The step of cDNA preamplification serves the purpose that the sensitivity of the assays is boosted. In one particular embodiment, said cDNA preamplification is carried out with a Forward primer having the following sequence from 5' to 3': TGGAGTGTGTGCTTTGCCACG (SEQ ID NO: 4) or with a variant of this sequence and a Reverse primer having the following sequence from 5' to 3': GTGCGAATACCTCGGACC (SEQ ID NO: 5) or with a variant of this sequence. While the forward primer is derived from the 5' adapter, the reverse primer is derived from the 3' adapter. These primer designs render the preamplification completely dependent on ligation of both the 5' and 3' adapters to exclusively preamplify the ligation product.

In this respect, it should be noted that the Reverse primer having the following sequence from 5' to 3':

GTGCGAATACCTCGGACC (SEQ ID NO: 5) is reverse complementary to at least a part of the 3' adapter sequence as described above. In particular, the Reverse primer is reverse complementary to nucleotides in the 3' positioned second stem sequence and in the loop sequence. As mentioned above, the 3' adapter sequence is preferably the following from 5' to 3': /5Phos/ CTCAGTGCAGGGTCCGAGGTATTCGCACTGAG(6-15x)N/3InvdT/(SEQ ID NO: 2), wherein "/5Phos/" indicates that the 5'-terminal nucleotide is phosphorylated, wherein one or more nucleotides in the underlined portion and/or one or more nucleotides in the double underlined portion are LNA enhanced, wherein (6-15x)N designates the sequence reverse complementary to a 3' terminal sequence of a target RNA, and wherein "/3InvdT/" stands for 3' inverted deoxynucleotide. Specifically, the LNA enhanced nucleotides are ribonucleotides.

In addition, it should be noted that the Forward primer having the following sequence from 5' to 3': TGGAGTGTGTGCTTTGCCACG (SEQ ID NO: 4) is instead reverse complementary to the DNA product produced from the 5' adapter in the reverse transcription reaction. As mentioned above, the 5' adapter sequence is preferably the following from 5' to 3':

(6-15x)NCGTGGCGTGGAGTGTGTGCTTTGCCA-rCrG (SEQ ID NO: 1), wherein "r" stands for ribonucleotide, wherein "(6-15x)N" designates the sequence reverse complementary to a 5' terminal sequence of a target RNA, and wherein one or more nucleotides in the underlined portion and/or one or more nucleotides in the double underlined portion are LNA enhanced. Specifically, the LNA enhanced nucleotides are ribonucleotides. Alternatively, the 5' adapter sequence is the following from 5' to 3':

(6-15x)NCGTGGCG/idSp/TGGAGTGTGTGCTTTGC-CArCrG (SEQ ID NO: 29), wherein "r" stands for ribonucleotide, wherein "(6-15x)N" designates the sequence reverse complementary to a 5' terminal sequence of a target RNA, wherein "idSp" stands for base lacking spacer, and wherein one or more nucleotides in the underlined portion and/or one or more nucleotides in the double underlined portion are LNA enhanced.

Any preamplification method may be used. In one preferred embodiment, the preamplification is carried out using a polymerase chain reaction (PCR). The preamplification using a PCR may be carried out as follows: 95° C. for 3 minutes, followed by 12 cycles at 95° C. for 15 seconds and at 58° C. for 4 minutes. The preamplification sample is subsequently hold at 4° C.

Subsequent to the preamplification or instead of the preamplification, an amplification reaction is carried out. The amplification requires a DNA polymerase, e.g. a Taq polymerase.

In one particular embodiment, the amplification reaction, is carried out with a Forward primer having the following sequence from 5' to 3': TGGAGTGTGTGCTTTGCCACG (SEQ ID NO: 4) or with a variant of this sequence and a Reverse primer having the following sequence from 5' to 3': GTGCGAATACCTCGGACC (SEQ ID NO: 5) or with a variant of this sequence (see above).

Any amplification method may be used.

Specifically, the amplification is carried out using a polymerase chain reaction (PCR).

More specifically, the PCR is selected from the group consisting of real-time PCR (quantitative PCR or qPCR), preferably Taq-man qPCR, multiplex PCR, nested PCR, high fidelity PR, fast PCR, hot start PCR, and GC-rich PCR.

Even more specifically, the TaqMan qPCR is carried out with a Forward primer having the following sequence from 5' to 3': TGGAGTGTGTGCTTTGCCACG (SEQ ID NO: 4) or with a variant of this sequence and a Reverse primer having the following sequence from 5' to 3': GTGCGAATACCTCGGACC (SEQ ID NO: 5) or with a variant of this sequence. While the forward primer is derived from the 5' adapter, the reverse primer is derived from the 3' adapter. These primer designs render the amplification completely dependent on ligation of both the 5' and 3' adapters to exclusively amplify the ligation product. The amplification using a Taq-man qPCR may be carried out as follows: 95° C. for 20 seconds, followed by 40 cycles at 95° C. for 1 second and 60° C. for 20 seconds. The amplification sample is subsequently hold at 4° C.

Still even more specifically, the TaqMan qPCR is carried out in the presence of a TaqMan probe. The sequence of the TaqMan probe depends on the sequence of the RNA target. The TaqMan probe is a hydrolysis probe that is designed to increase the specificity of quantitative PCR. In general, the TaqMan probe principle relies on the 5'-3' exonuclease activity of the Taq polymerase to cleave a dual-labeled probe during hybridization to the complementary target sequence and fluorophore-based detection. As in other quantitative PCR methods, the resulting fluorescence signal permits quantitative measurements of the accumulation of the product during the exponential stages of the PCR. However, the TaqMan probe significantly increases the specificity of the detection.

The Forward primer variant as described above has a sequence having at least 80%, preferably 85%, more preferably 90%, even more preferably 95%, still even more preferably 99%, e.g. 80, 81, 82, 83, 84, 85, 86, 87, 88, 89, 90, 91, 92, 93, 94, 95, 96, 97, 98, or 99%, sequence identity to the sequence according to SEQ ID NO: 4. Such a Forward primer variant is still capable of binding the DNA product produced from the 5' adapter in the reverse transcription reaction. In other words, the Forward primer variant must have at least in part, e.g. over a length of at least 10, 11, 12, 13, 14, 15, 16, 17, 18, 19, 20, or of 21 nucleotides, the same sequence as the 5' adapter. In particular, the sequences are identical, e.g. over a length of at least 10, 11, 12, 13, 14, 15, 16, 17, 18, 19, 20, or 21 nucleotides, in the loop region and in the 3' positioned second stem sequence of the 5' adapter. The skilled person can readily assess whether a Forward primer variant is still capable binding the DNA product produced from the 5' adapter in the reverse transcription reaction. For example, the experimental section provides sufficient information in this respect.

In addition, the Reverse primer variant as described above has a sequence having at least 80%, preferably 85%, more preferably 90%, even more preferably 95%, still even more preferably 99%, e.g. 80, 81, 82, 83, 84, 85, 86, 87, 88, 89, 90, 91, 92, 93, 94, 95, 96, 97, 98, or 99%, sequence identity to the sequence according to SEQ ID NO: 5. Such a Reverse primer variant is still capable of binding the 3' adapter sequence and allowing cDNA preamplification/amplification. The skilled person can readily assess whether a Reverse primer variant is still capable of binding the 3' adapter sequence and allowing cDNA preamplification/amplification. For example, the experimental section provides sufficient information in this respect.

In the methods according to the fourth and/or fifth aspect of the present invention, the sample is preferably a biological sample. The biological sample may be any sample having a biological origin. For example, the biological sample may be a body fluid sample, e.g. a blood sample or urine sample, or a tissue sample, e.g. a tissue biopsy sample. Biological samples may be mixed or pooled, e.g. a sample may be a mixture of a blood sample and a urine sample.

The body fluid sample may be a urine sample, blood sample, sputum sample, breast milk sample, cerebrospinal fluid (CSF) sample, cerumen (earwax) sample, gastric juice sample, mucus sample, lymph sample, endolymph fluid sample, perilymph fluid sample, peritoneal fluid sample, pleural fluid sample, saliva sample, sebum (skin oil) sample, semen sample, sweat sample, tears sample, cheek swab, vaginal secretion sample, liquid biopsy, or vomit sample including components or fractions thereof. The term "body fluid sample" also encompasses body fluid fractions, e.g. blood fractions, urine fractions or sputum fractions. Body fluid samples may be mixed or pooled. Thus, a body fluid sample may be a mixture of a blood and a urine sample or a mixture of a blood and cerebrospinal fluid sample.

More preferably, the biological sample is a blood sample. Even more preferably, the blood sample is a whole blood or a blood fraction, preferably blood cells (e.g. erythrocytes, leukocytes, and/or thrombocytes), serum, or plasma. For example, the blood cell fraction encompasses erythrocytes, leukocytes, and/or thrombocytes. The whole blood sample may be collected by means of a blood collection tube. It is, for example, collected in a PAXgene Blood RNA tube, in a Tempus Blood RNA tube, in an EDTA-tube, in a Na-citrate tube, Heparin-tube, or in a ACD-tube (Acid citrate dextrose). The whole blood sample may also be collected by means of a bloodspot technique, e.g. using a Mitra Microsampling Device. This technique requires smaller sample volumes, typically 45-60 ul for humans or less. For example, the whole blood may be extracted from the patient via a finger prick with a needle or lancet. Thus, the whole blood sample may have the form of a blood drop. Said blood drop is then placed on an absorbent probe, e.g. a hydrophilic polymeric material such as cellulose, which is capable of absorbing the whole blood. Once sampling is complete, the blood spot is dried in air before transferring or mailing to labs for processing. Because the blood is dried, it is not considered hazardous. Thus, no special precautions need be taken in handling or shipping. Once at the analysis site, the desired components, e.g. miRNAs, are extracted from the dried blood spots into a supernatant which is then further analyzed.

In the methods according to the fourth and/or fifth aspect of the present invention, the sample may also be a sample containing total RNA. Particularly, total RNA includes RNA having a length of <200 nucleotides such as a miRNA or a miRNA isoform (an isomiR). Specifically, the sample used in the methods according to the fourth and/or fifth aspect of the present invention contains cellular total RNA. Particularly, cellular total RNA includes RNA having a length of <200 nucleotides such as a miRNA or a miRNA isoform (an isomiR). The cellular total RNA may be obtained from blood cells, e.g. erythrocytes, leukocytes, and/or thrombocytes.

In a sixth aspect, the present invention relates to a method of diagnosing a disease or condition in a patient comprising the steps of:
  (ia) carrying out the methods according to the fourth and/or fifth aspect, thereby determining the presence or absence of the target RNA, and
  (iia) diagnosing whether the patient is afflicted by the disease or condition based on the presence or absence of the target RNA, or
  (ib) carrying out the methods according to the fourth and/or fifth aspect, thereby quantifying the target RNA,
  (iib) comparing the quantified target RNA with a reference, and
  (iiib) diagnosing whether the patient is afflicted by the disease or condition based on the comparison.

Thus, the present invention relates to a method of diagnosing a disease or condition in a patient comprising the steps of:
  (i) carrying out the methods according to the fourth and/or fifth aspect, thereby determining the presence or absence of the target RNA, and
  (ii) diagnosing whether the patient is afflicted by the disease or condition based on the presence or absence of the target RNA.

Accordingly, the presence or absence of the target RNA is indicative for the disease or condition.

For example, the patient is diagnosed to be afflicted by the disease or condition, if the target RNA is present or absent. Alternatively, the patient is diagnosed to be not afflicted by the disease or condition, if the target RNA is present or absent.

Alternatively, the present invention relates to a method of diagnosing a disease or condition in a patient comprising the steps of:
  (i) carrying out the methods according to the fourth and/or fifth aspect, thereby quantifying the target RNA,
  (ii) comparing the quantified target RNA with a reference, and
  (iii) diagnosing whether the patient is afflicted by the disease or condition based on the comparison.

Particularly, the reference is a reference target RNA. More particularly, the reference is a reference obtained from one or more healthy (control) subjects. Even more particularly, the reference is the quantified reference target RNA determined in one or more healthy (control) subjects. If two or more healthy (control) subjects have been tested, the quantity of the reference target RNA may be indicated as mean value. For example, the patient is diagnosed to be afflicted by the disease or condition, if the quantified target RNA is above or below the quantified reference target RNA, e.g. obtained from one or more healthy (control) subject. Alternatively, the patient is diagnosed to be not afflicted by the disease or condition, if the quantified target RNA is above or below the quantified reference target RNA, e.g. obtained from one or more healthy (control) subjects. The reference may also be a reference obtained from one or more (control) subjects suffering from a disease or condition.

In one preferred embodiment, the quantified target RNA is a miRNA or a miRNA isoform (an isomiR). In one another preferred embodiment, the quantified reference target RNA is a miRNA or a miRNA isoform (an isomiR). Specifically, the target RNA and the reference target RNA are identical, i.e. from the same RNA type, e.g. both RNAs are miRNAs.

In one (additional or alternative) preferred embodiment, the disease is selected from the group consisting of neurodegenerative disease, an autoimmune disease, an infectious disease, and cancer. In one more preferred embodiment,
  (i) the neurodegenerative disease is selected from the group consisting of Alzheimer's disease (AD) and other dementias, Parkinson's disease (PD) and PD-related diseases, Prion disease, Motor neurone diseases (MND), Huntington's disease (HD), Spinocerebellar ataxia (SCA), Spinal muscular atrophy (SMA), AIDS dementia complex, and atherosclerosis,
  (ii) the autoimmune disease is selected from the group consisting of diabetes, rheumatoid arthritis (RA), multiple sclerosis (MS), systemic lupus erythematosus (lupus), Graves' disease, Sjögren's syndrome, Hashimoto's thyroiditis, Myasthenia gravis, Vasculitis, Pernicious anemia, and Celiac disease,
(iii) the infectious disease is selected from the group consisting of viral infection, preferably chronic or persistent viral infection, bacterial infection, parasitic infection, or
(iv) the cancer is selected from the group consisting of skin cancer, nasopharyngeal cancer, neuroendrocrine cancer, lung cancer, colon cancer, urothelial cancer, bladder cancer, liver cancer, ovarian cancer, gastric cancer, esophageal cancer, pancreatic cancer, kidney cancer, stomach cancer, esophageal cancer, breast cancer, renal cancer, head and neck cancer, brain cancer, lymphatic cancer, blood cancer, squamous cell cancer, laryngeal cancer, retina cancer, prostate cancer, cervical cancer, uterine cancer, testicular cancer, bone cancer, lymphoma, and leukemia.

In a seventh aspect, the present invention relates to a kit comprising
the 5' adapter according to the first aspect, and
the 3' adapter according to the second aspect, or
the combination according to the third aspect.

In one preferred embodiment, the kit further comprises a double stranded RNA ligase, preferably a T4 RNA ligase 2 (Rnl2) or a Kod1 ligase. In this case, the kit preferably further comprises instructions on how to carry out the method according to the fourth aspect. The kit with this composition preferably further allows to conduct the method according to the fourth aspect.

In one (additional or alternative) preferred embodiment, the kit further comprises
a reverse transcriptase (RT), preferably a Maxima H-RT or a Tth polymerase, and a RT primer allowing reverse transcription of the target RNA in order to obtain a cDNA product from the target RNA, and/or
a DNA polymerase, preferably a Taq polymerase, and a Forward primer and/or a Reverse primer allowing the preamplification and/or amplification of the cDNA.

In this case, the kit preferably further comprises instructions on how to carry out the method according to the fifth aspect. The kit with this composition preferably further allows to conduct the method according to the fifth aspect.

Optionally, the kit further comprises a TaqMan probe.

As to the specific RT, Forward and/or Reverse primers, it is referred to the fifth aspect of the present invention.

In one further (additional or alternative) preferred embodiment, the kit further comprises a reference. In this case, the kit preferably further comprises instructions on how to carry out the method according to the sixth aspect. The kit with this composition preferably further allows to conduct the method according to the sixth aspect.

As to the reference, it is referred to the sixth aspect of the present invention.

In view of the above, the kit comprises in one more preferred embodiment the following components:
(i) the 5' adapter according to the first aspect and the 3' adapter according to the second aspect or the combination according to the third aspect,
(ii) a reverse transcriptase (RT), preferably a Maxima H-RT or a Tth polymerase, and a RT primer allowing reverse transcription of the target RNA in order to obtain a cDNA product from the target RNA, and/or
(iii) a DNA polymerase, preferably a Taq polymerase, and a Forward primer and/or a Reverse primer allowing the preamplification and/or amplification of the cDNA.

Optionally, the kit further comprises a TaqMan probe.

The kit comprises in one even more preferred embodiment the following components:
(i) the 5' adapter
having the following sequence from 5' to 3':
(6-15×)NCGTGGCGTGGAGTGTGTGCTTTGCCA-rCrG (SEQ ID NO: 1), wherein "r" stands for ribonucleotide, wherein "(6-15×)N" designates the sequence reverse complementary to a 5' terminal sequence of a target RNA, and wherein one or more nucleotides in the underlined portion and/or one or more nucleotides in the double underlined portion are LNA enhanced, or a variant of this sequence, and
the 3' adapter
having the following sequence from 5' to 3':
/5Phos/CTCAGTGCAGGGTCCGAGGTAT-TCGCACTGAG(6-15×)N/3InvdT/(SEQ ID NO: 2), wherein "/5Phos/" indicates that the 5'-terminal nucleotide is phosphorylated, wherein one or more nucleotides in the underlined portion and/or one or more nucleotides in the double underlined portion are LNA enhanced, wherein "(6-15×)N" designates the sequence reverse complementary to a 3' terminal sequence of a target RNA, and wherein "/3InvdT/" stands for 3' inverted deoxynucleotide, or a variant of this sequence,
(ii) a reverse transcriptase (RT), preferably a Maxima H-RT or a Tth polymerase, and a RT primer having a sequence according to SEQ ID NO: 3 or a variant of this sequence, and/or
(iii) a DNA polymerase, preferably a Taq polymerase, and a Forward primer having a sequence according to SEQ ID NO: 4 or a variant of this sequence and/or a Reverse primer having a sequence according to SEQ ID NO: 5 or a variant of this sequence.

Optionally, the kit further comprises a TaqMan probe.

Alternatively, the above-mentioned 5' adapter is replaced by a 5' adapter having the following sequence from 5' to 3':
(6-15×)NCGTGGCG/idSp/TGGAGTGTGTGCTTTGC-CArCrG (SEQ ID NO: 29), wherein "r" stands for ribonucleotide, wherein "(6-15×)N" designates the sequence reverse complementary to a 5' terminal sequence of a target RNA, wherein "idSp" stands for base lacking spacer, and wherein one or more nucleotides in the underlined portion and/or one or more nucleotides in the double underlined portion are LNA enhanced, or a variant of this sequence.

The kit comprises in one still even more preferred embodiment the following components:
(i) the 5' adapter
having the following sequence from 5' to 3':
(6-15×)NCGTGGCGTGGAGTGTGTGCTTTGCCA-rCrG (SEQ ID NO: 1), wherein "r" stands for ribonucleotide, wherein "(6-15×)N" designates the sequence reverse complementary to a 5' terminal sequence of a target RNA, and wherein one or more (e.g. 1, 2, or 3) of the nucleotides in bold letters are LNA enhanced, or a variant of this sequence, and
the 3' adapter
having the following sequence from 5' to 3':
/5Phos/CTCAGTGCAGGGTCCGAGGTAT-TCGCACTGAG(6-15×)N/3InvdT/(SEQ ID NO: 2), wherein "/5Phos/" indicates that the 5'-terminal nucleotide is phosphorylated, wherein one or more (e.g. 1, 2, or 3) of the nucleotides in bold letters are LNA enhanced, wherein "(6-15×)N" designates the sequence reverse complementary to a 3' terminal sequence of a target RNA, and wherein "/3InvdT/" stands for 3' inverted deoxynucleotide, or a variant of this sequence, (ii) a reverse transcriptase (RT), preferably a Maxima H-RT or a Tth polymerase, and a RT primer having a sequence according to SEQ ID NO: 3 or a variant of this sequence, and/or (iii) a DNA polymerase, preferably a Taq polymerase, and a Forward primer having a sequence according to SEQ ID NO: 4 or a variant of this sequence and/or a Reverse primer having a sequence according to SEQ ID NO: 5 or a variant of this sequence.

Optionally, the kit further comprises a TaqMan probe.

Alternatively, the above-mentioned 5' adapter is replaced by a 5' adapter having the following sequence from 5' to 3':

(6-15×)NCGTGGCG/idSp/TGGAGTGTGTGCTTTGC-CArCrG (SEQ ID NO: 29), wherein "r" stands for ribonucleotide, wherein "(6-15×)N" designates the sequence reverse complementary to a 5' terminal sequence of a target RNA, wherein "idSp" stands for base lacking spacer, and wherein one or more (e.g. 1, 2, or 3) of the nucleotides in bold letters are LNA enhanced, or a variant of this sequence.

As to the specific variants as described above, it is referred to the first, second, fourth and fifth aspect of the present invention.

The kit may further comprise (i) one or more containers for the different components of the kit, and/or (ii) a data carrier.

Said data carrier may be a non-electronical data carrier, e.g. a graphical data carrier such as an information leaflet, an information sheet, a bar code or an access code, or an electronical data carrier such as a floppy disk, a compact disk (CD), a digital versatile disk (DVD), a microchip or another semiconductor-based electronical data carrier. The access code may allow the access to a database, e.g. an internet database, a centralized, or a decentralized database. The access code may also allow access to an application software that causes a computer to perform tasks for computer users or a mobile app which is a software designed to run on smartphones and other mobile devices.

Said data carrier may further comprise a reference as described in the context of the sixth aspect. In case that the data carrier comprises an access code which allows the access to a database, said reference is deposited in this database.

In addition, the data carrier may comprise information or instructions on how to carry out the methods of the fourth to sixth aspect of the present invention.

Said kit may also comprise materials desirable from a commercial and user standpoint including a buffer(s), a reagent(s) and/or a diluent(s) which might be possible to carry out the methods of the fourth to sixth aspect of the present invention. In particular, the kit may also comprise buffers and components for carrying out annealing and ligation of the two adapters to a target RNA, buffers and components for carrying out reverse transcription of the target RNA, and/or buffers and components for carrying out preamplification and/or amplification of the target RNA.

Various modifications and variations of the invention will be apparent to those skilled in the art without departing from the scope of invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art in the relevant fields are intended to be covered by the present invention.

BRIEF DESCRIPTION OF THE FIGURES

The following Figures are merely illustrative of the present invention and should not be construed to limit the scope of the invention as indicated by the appended claims in any way.

FIG. 1: Shows an exemplarily schematic hybrid structure of 5' adapter, 3' adapter and target miRNA. In this structure, the 5' adapter has the following sequence: 5' ATC-TACGGGTTCGTGGCGTGGAGTGTGTGCTTTGCCA-rCrG 3' (SEQ ID NO: 6), wherein "r" stands for ribonucleotide, wherein the sequence in bold letters designates the sequence reverse complementary to the 5' terminal sequence of the target RNA miR-100-5p, and wherein one or more nucleotides in the underlined portion and/or one or more nucleotides in the double underlined portion are LNA enhanced. In this structure, the 3' adapter has the following sequence: 5'/5Phos/CTCAGTGCAGGGTCCGAGGTAT-TCGCACTGAGCACAAGT/3InvdT/3' (SEQ ID NO: 7), wherein "/5Phos/" indicates that the 5'-terminal nucleotide is phosphorylated, wherein one or more nucleotides in the underlined portion and/or one or more nucleotides in the double underlined portion are LNA enhanced, wherein the sequence in bold letters designates the sequence reverse complementary to a 3' terminal sequence of the target RNA miR-100-5p, and wherein "/3InvdT/" stands for 3' inverted deoxynucleotide. The target RNA miR-100-5p has the following sequence: 5' AACCCGUAGAUCCGAACUUGUG 3' (SEQ ID NO: 8). Reverse complementary sequences to the 5'/3' adapters are indicated in bold letters.

FIGS. 2-A-2D: Results of commercial assays and DB PCR assays on the testbed of 8 variants of miR-100-5p. In the columns are the RNA templates listed which were used, in the rows the respective assays. The numbers depicted are Ct values as provided by the ABI Flex6 qPCR instrument. The lower the Ct number is, the more RNA is detected in the sample. The highlight in green indicates where the signal is only expected.

FIG. 3: Results of the DB PCR assay experiment done similarly as shown on FIGS. 2A-2D, but on the 60 amol of the RNA template and 7 cycles of pre-amplification.

FIG. 4: Sequence of target RNA miR-100-5p and of variants of target RNA miR-100-5p used for the analyses show. in the FIGS. 1 and 2A-2D.

FIG. 6: Overview of the 5' and 3' adapters, reverse transcription (RT) primers, Forward and Reverse primers and TaqMan probes used for the different miRNAs in the experimental setup.

FIG. 7: Specific combinations of miRNA variant, 5' adapter, 3' adapter and TaqMan probe.

EXAMPLES

Figure 2A:
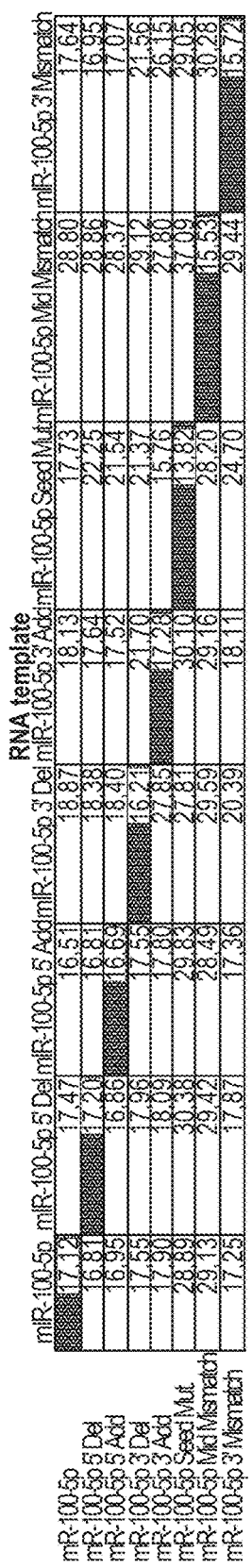
FIG. 2A. LNA-based primer commercial assay were tested on 60 amol of the RNA template.
Figure 2B:
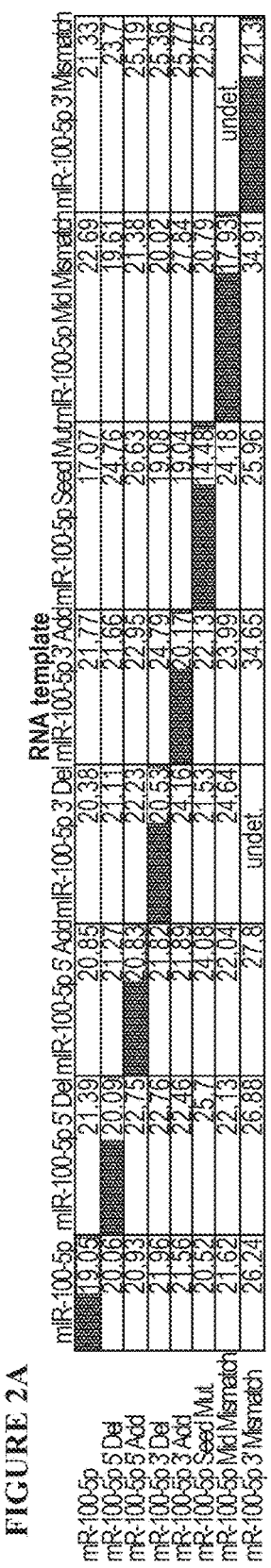
FIG. 2B. Stem-loop primer-based commercial assay was tested on 60 amol of the RNA template.
Figure 2C:
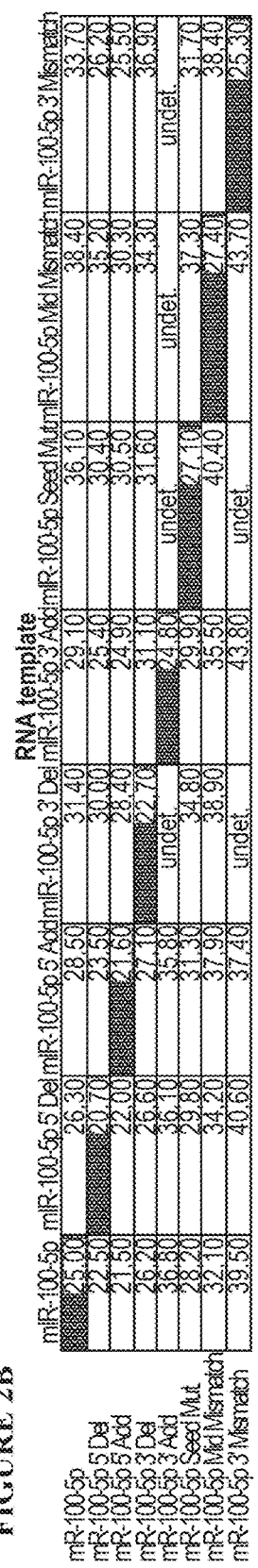
FIG. 2C. Commercial assay based on primer-probe hybrid was tested on 2 pmol of the RNA template.
Figure 2D:
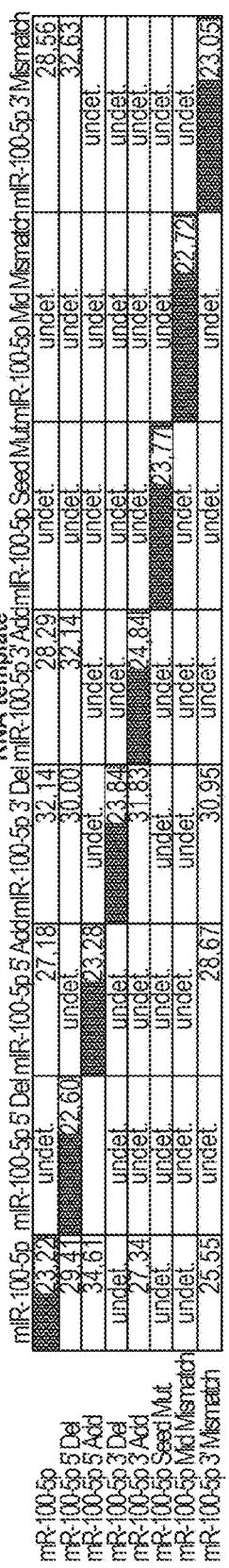
FIG. 2D. DB-PCR assay without pre-amplification step was tested on the 10 fmol of the RNA template.

The examples given below are for illustrative purposes only and do not limit the invention described above in any way.

1. Materials & Methods

First, adapters are denaturated and renaturated such they form required stem loop-like structures. RNA is denaturated separately, mixed with adapters and used for the ligation by Rnl2. Subsequently, RT primer aligning to the 3' adapter is used for the cDNA production. cDNA is pre-amplified (e.g. using Biorad Pre-amp Mix) and then used for the qPCR with a reverse primer aligning to the 5' end of first strand cDNA and forward primer complementary to the 3' end of the first strand cDNA. Finally, a TaqMan probe is used for the detection of the specific signal in qPCR.

An exemplarily 5' adapter (SEQ ID NO: 6) and an exemplarily 3' adapter (SEQ ID NO: 7) are shown in FIG. 1. These adapters target the miR-100-5p (SEQ ID NO: 8).

Protocol Details:

Adapters, primers and probes were designed such that these can recognize and be specific for the miR-100-5p and its variants (listed in FIG. 3). Synthetic miRs were ordered in 5' phosphorylated form. The full list of adapters, probes and primers is listed in the FIG. 6. All oligos were ordered in dried form.

All oligos were diluted in nuclease-free water to concentration of 100 µM and stored in −20° C. in dark. Adapters were then prepared as follows:

| Adapter preparation | | | |
|---|---|---|---|
| Adapters are first separately denaturated and then re-natured in a 1x annealing buffer Recipe 10x TNE annealing buffer | | | |
| | MW | for 200 ml: | |
| 100 mM TRIS HCl 7.5 | 121.14 | 2.42 g | in 100 ml, then pH adjusted (ca 2.5 ml HCl) |
| 500 mM NaCl | 58.44 | 5.84 g | |
| 1 mM EDTA | 292 | 58 mg | |
| | | then volume adjusted to 200 ml with DEPC water | |
| Denaturation + renaturation – resulting in 5 µM adapter working stock | | | |
| Adapter (100 µM stock) | 2 µl | | |
| 10x TNE annealing buffer | 4 µl | | |
| Water | 34 µl | | |
| Total | 40 µl | | |
| Heat the mixture to 82 C. for 2 min | | | |
| Ramp down 0.1 C./sec to 4 C. | | | |
| Store in −20 C. | | | |

Next, RNA was prepared by denaturation. Either indicate amount of PAXgene total RNA was used or indicated amount of synthetic miR-100-5p wt and variants were used in equimolar pool. The RNA was denaturated for 2 min at 70° C. and placed immediately on ice.

Next, ligation reaction was prepared with following components. After the reaction was well mixed, it was incubated 1 hour at 37° C.

| Ligation of the adapters to RNA Both adapters ale ligated at the same time Ligation | |
|---|---|
| Denaturated RNA | 5 µl |
| 5' Adapter (5 µM) | 1 µl |
| 3' Adapter (5 µM) | 1 µl |
| PEG8000 (50%) | 2 µl |
| 10x RNA ligation buffer | 2 µl |
| T4 Rnl2 (10 U/µl) | 1 µl |
| ATP 10 mM | 2 µl |
| Water | 6 µl |
| Total | 21 µl |

Next, ligated RNA was used for reverse transcription reaction using the RT primer, as indicated in the following protocol.

| Reverse transcription | |
|---|---|
| Ligated RNA | 6 µl |
| dNTPs [10 mM each] | 0.5 µl |
| RT Primer [5 µM] | 1 µl |
| Total | 7.5 µl |
| Incubate 5 min at 65° C. and cool immediately on ice | |
| Add following to the previous mixture | |
| 5x Maxima RT Buffer | 2 µl |
| RI | 0.25 µl |
| Maxima H-RT (200 U/µl) | 0.25 µl |
| Total volume | 10 µl |
| incubate at 55° C. for 30 min, followed by 3 min incubation at 85° C and store at 4° C. store in −20 C. | |

After reverse transcription, the cDNA was used for a pre-amplification reaction using commercial Pre-amplification Master mix (BioRad). Afterwards, the pre-amplified cDNA was diluted and stored in −20° C.

| | |
|---|---|
| cDNA | 5 µl |
| 2x Pre-Amp Master Mix | 6 µl |
| Forward Primer [5 µM] | 0.12 µl |
| Reverse Primer [5 µM] | 0.12 µl |
| Nuclease-free water | 0.76 µl |
| Total volume | 12 µl |

| Run in the thermocycler as follows: | | |
|---|---|---|
| Temperature | Time | cycles |
| 95° C. | 3 min | |
| 95° C. | 15 sec | 1.2x |
| 58° C. | 4 min | |
| 4° C. | hold | |
| Dilute the pre-amplified cDNA 1:5 by adding 48 µl of water Store in −20 C. | | |

Finally, qPCR assays using diluted cDNA was used including Taqman probes. The reaction was run in ABI Flex 6 machine in 384 well format.

| Taq-man qPCR | |
|---|---|
| Diluted cDNA | 2 µl |
| TaqMan probe (1 µM stock) | 1 µl |
| Forward primer (5 µM stock) | 0.4 µl |
| Reverse primer (5 µM stock) | 0.4 µl |
| 2x Taqman Fast Advanced Master Mix | 5 µl |
| Water | 1.4 µl |
| Total | 10 µl |
| Use a thermocycler program as such: 95° C. for 20 s, followed by 40 cycles of 95° C. for 1 s and 60° C. for 20 s. | |

2. Results

The original DB PCR protocol was improved in the ligation aspects. It was then used for a comparison with available major commercial assays as showed in FIGS. 2A-2D. It could clearly be shown that the "improved Dumbbell (DB) PCR" protocol had superior specificity compared to the other assays. The protocol was further optimized with a pre-amplification step to create an "advanced DB PCR". In this way, high sensitivity could be reached while not losing specificity (FIG. 3).

Figure 5A:
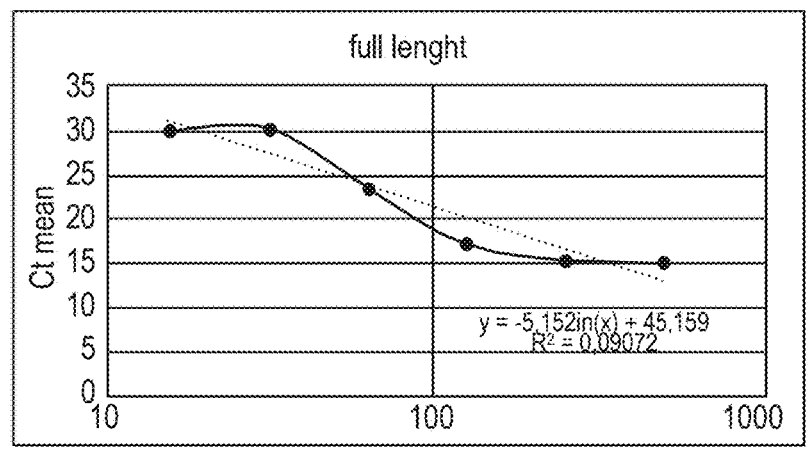
FIGS. 5A-5B: Detection of the endogenous miR-100-5p wt (FIG. 5A) and 3' deletion (FIG. 5B) in the PAXgene RNA sample. The amount of RNA sample added into the reaction is indicated as well as resulting Ct values of DB PCR with 7 cycles of the pre-amplification.
Figure 5B:
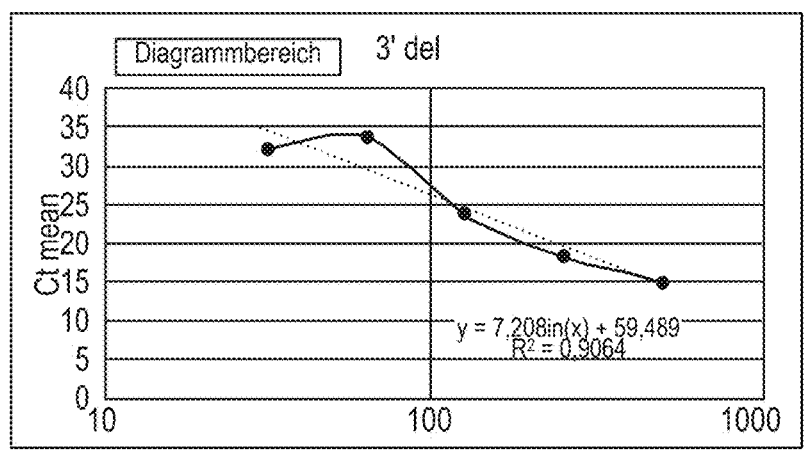

It is important to note that the assay can be used on biological sources of RNA such as clinical samples, e.g. PAXgene whole blood RNA sample. The original DB PCR protocol is not able to detect miR-100-5p in human PAXgene RNA sample (data not shown). Advanced DB PCR protocol can detect miR-100-5p in PAXgene RNA sample (FIGS. 5A-5B), and that in its wt or canonical form, as well as 3' deletion variant.

The sequences of the specific adapters and Taqman probes used for the detection are shown in the FIG. 6. The combinations of the adapters and probes used for the discrimination assays are shown in the FIG. 7.

3. Sequences of the Adapters and Primers (in 5'→3' Orientation)

5' Adapter from 5' to 3':

(6-15×)NCGTGGCGTGGAGTGTGTGCTTTGCCA-rCrG (SEQ ID NO: 1), wherein "r" stands for ribonucleotide, wherein "(6-15×)N" designates the sequence reverse complementary to a 5' terminal sequence of a target RNA, and wherein one or more nucleotides in the underlined portion and/or one or more nucleotides in the double underlined portion are LNA enhanced. An exemplarily 5' adapter targeting miR-100-5p has a nucleotide sequence according to SEQ ID NO: 6.

3' Adapter from 5' to 3':

/5Phos/CTCAGTGCAGGGTCCGAGGTATTCGCACT-GAG(6-15×)N/3InvdT/(SEQ ID NO: 2), wherein "/5Phos/" indicates that the 5'-terminal nucleotide is phosphorylated, wherein one or more nucleotides in the underlined portion and/or one or more nucleotides in the double underlined portion are LNA enhanced, wherein (6-15×)N designates the sequence reverse complementary to a 3' terminal sequence of a target RNA, and wherein "/3InvdT/" stands for 3' inverted deoxynucleotide. An exemplarily 3' adapter targeting miR-100-5p has a nucleotide sequence according to SEQ ID NO: 7.

```
RT primer from 5' to 3':
                                        (SEQ ID NO: 3)
CTCAGTGCGAATACCTCGGACCCT Forward primer from 5' to 3':
                                        (SEQ ID NO: 4)
TGGAGTGTGTGCTTTGCCACG Reverse primer from 5' to 3':
                                        (SEQ ID NO: 5)
GTGCGAATACCTCGGACC
```

The invention claimed is:

1. A combination comprising
a 5' adapter comprising in the following order from 5' to 3'
   (i) a 5' terminal nucleotide sequence comprising 6 to 15 deoxynucleotides, wherein said 6 to 15 deoxynucleotides are reverse complementary to a 5'-terminal sequence of a target RNA, and
   (ii) a nucleotide sequence capable of forming a stem-loop structure containing a loop and a double-stranded stem, wherein at least 2 nucleotides at its 3' end are ribonucleotides or modified ribonucleotides,
and
a 3' adapter comprising in the following order from 5' to 3'
   (i) a nucleotide sequence capable of forming a stem-loop structure containing a loop and a double-stranded stem, wherein the 5'-terminal nucleotide is phosphorylated; and
   (ii) a 3' terminal nucleotide sequence comprising 6 to 15 deoxynucleotides, wherein said 6 to 15 deoxynucleotides are reverse complementary to a 3'-terminal sequence of a target RNA, and wherein the 3' terminal deoxynucleotide is an inverted deoxynucleotide,
wherein the stem sequence of the stem-loop structure in the 5' adapter or the 3' adapter comprises between 2 to 5 locked nucleotides.

2. A method of ligating two adapters to a target RNA in a sample, comprising the steps of:
   (i) providing a composition comprising a denatured target RNA in a sample and the combination of claim 1, wherein the 5' adapter and the 3' adapter are renatured and annealed to the target RNA,
and
   (ii) ligating the 5' adapter and the 3' adapter to the target RNA using a double-stranded RNA ligase, thereby producing a ligation product.

3. The method of claim 2, wherein
   (1) the denatured target RNA is produced by heating the target RNA at between 65° C. and 75° C. for between 1 to 3 minutes,
   (2) the renatured 5' adapter is produced by denaturing the 5' adapter at between 75° C. and 85° C. for between 1 to 3 minutes, and renaturing the 5' adapter by cooling down to 4° C., and/or
   (3) the renatured 3' adapter is produced by denaturing the 3' adapter at between 75° C. and 85° C. for between 1 to 3 minutes, and renaturing the 3' adapter by cooling down to 4° C.

4. The method of claim 2, wherein the renatured 5' and 3' adapters are produced separately and in the absence of target RNA.

5. The method of claim 2, further comprising, after step (ii), the steps of:
   (iii) reverse transcribing the ligation product, thereby obtaining a cDNA product from the target RNA, and
   (iv) amplifying the cDNA, thereby determining and/or quantifying the target RNA.

6. The combination of claim 1, wherein in the 5' adapter the stem-loop structure comprises a 5'-positioned first stem sequence and a 3'-positioned second stem sequence that are reverse complementary to each other, and wherein each one of the 5'-positioned first stem sequence and the 3'-positioned second stem sequence has a length of between 5 to 10 nucleotides.

7. The combination of claim 6, wherein the 5'-positioned first stem sequence and the 3'-positioned second stem sequence have the same length.

8. The combination of claim 1, wherein the stem sequence of the stem-loop structure in the 5' adapter comprises between 2 to 5 locked nucleotides.

9. The combination of claim 1, wherein the stem sequence of the stem-loop structure in the 3' adapter comprises between 2 to 5 locked nucleotides.

10. A kit comprising
a first container containing:
(A) a 5' adapter comprising in the following order from 5' to 3'
   (i) a 5' terminal nucleotide sequence comprising 6 to 15 deoxynucleotides, wherein said 6 to 15 deoxynucleotides are reverse complementary to a 5'-terminal sequence of a target RNA; and
   (ii) a nucleotide sequence capable of forming a stem-loop structure containing a loop and a double-stranded stem, wherein at least 2 nucleotides at its 3' end are ribonucleotides or modified ribonucleotides,
and
a second container containing:
(B) a 3' adapter comprising in the following order from 5' to 3'
   (i) a nucleotide sequence capable of forming a stem-loop structure containing a loop and a double-stranded stem, wherein the 5'-terminal nucleotide is phosphorylated; and
   (ii) a 3' terminal nucleotide sequence comprising 6 to 15 deoxynucleotides, wherein said 6 to 15 deoxynucleotides are reverse complementary to a 3'-terminal sequence of a target RNA, and wherein the 3' terminal deoxynucleotide is an inverted deoxynucleotide,
wherein the stem sequence of the stem-loop structure in the 5' adapter or the 3' adapter comprises between 2 to 5 locked nucleotides;

or a container containing (A) and (B).

11. The kit of claim 10, wherein in the 3' adapter the stem-loop structure comprises a 5'-positioned first stem sequence and a 3'-positioned second stem sequence that are reverse complementary to each other, and wherein each one of the 5'-positioned first stem sequence and the 3'-positioned second stem sequence has a length of between 5 to 10 nucleotides.

12. The kit of claim 11, wherein the 5'-positioned first stem sequence and the 3'-positioned second stem sequence have the same length.

13. The kit of claim 10, wherein the stem sequence of the stem-loop structure in the 5' adapter comprises between 2 to 5 locked nucleotides.

14. The kit of claim 10, wherein the stem sequence of the stem-loop structure in the 3' adapter comprises between 2 to 5 locked nucleotides.

\* \* \* \* \*

SEQUENCE LISTING

```
Sequence total quantity: 29
SEQ ID NO: 1              moltype = DNA  length = 43
FEATURE                   Location/Qualifiers
misc_feature              1..43
                          note = 5' adapter
misc_difference           1..9
                          note = positions can be absent
misc_difference           1..9
                          note = n is a, c, g, t or u
misc_difference           10..15
                          note = n is a, c, g, t or u
modified_base             16..21
```

```
                         mod_base = OTHER
                         note = Between 1 and 6 nucleotides in positions 16 to 21
                          can beLNA-enhanced
modified_base            38..43
                         mod_base = OTHER
                         note = Between 1 and 6 nucleotides in positions 38 to 43
                          can beLNA-enhanced
misc_difference          16..21
                         note = Between 1 and 6 nucleotides in positions 16 to 21
                          can beLNA-enhanced
misc_difference          38..43
                         note = Between 1 and 6 nucleotides in positions 38 to 43
                          can beLNA-enhanced
misc_feature             1..41
                         note = Bases are DNA
misc_feature             42..43
                         note = Bases are RNA
source                   1..43
                         mol_type = other DNA
                         organism = synthetic construct
SEQUENCE: 1
nnnnnnnnnn nnnnncgtgg cgtggagtgt gtgctttgcc acg                             43

SEQ ID NO: 2             moltype = DNA   length = 48
FEATURE                  Location/Qualifiers
misc_feature             1..48
                         note = 3' adapter
modified_base            1
                         mod_base = OTHER
                         note = This nucleotide is 5' terminally phosphorylated
modified_base            1..8
                         mod_base = OTHER
                         note = Between 1 and 8 nucleotides in positions 1 to 8 can
                          beLNA-enhanced
modified_base            25..32
                         mod_base = OTHER
                         note = Between 1 and 8 nucleotides in positions 25 to 32
                          can beLNA-enhanced
misc_difference          1..8
                         note = Between 1 and 8 nucleotides in positions 1 to 8 can
                          beLNA-enhanced
misc_difference          25..32
                         note = Between 1 and 8 nucleotides in positions 25 to 32
                          can beLNA-enhanced
misc_difference          33..38
                         note = n is a c g or t
misc_difference          39..47
                         note = Positions may be absent
variation                39..47
                         note = n is a c g t or u
modified_base            48
                         mod_base = OTHER
                         note = This nucleotide is a 3' inverted deoxynucleotide
source                   1..48
                         mol_type = other DNA
                         organism = synthetic construct
SEQUENCE: 2
ctcagtgcag ggtccgaggt attcgcactg agnnnnnnnn nnnnnnnt                       48

SEQ ID NO: 3             moltype = DNA   length = 24
FEATURE                  Location/Qualifiers
misc_feature             1..24
                         note = RT primer
source                   1..24
                         mol_type = other DNA
                         organism = synthetic construct
SEQUENCE: 3
ctcagtgcga atacctcgga ccct                                                 24

SEQ ID NO: 4             moltype = DNA   length = 21
FEATURE                  Location/Qualifiers
misc_feature             1..21
                         note = Forward primer
source                   1..21
                         mol_type = other DNA
                         organism = synthetic construct
SEQUENCE: 4
tggagtgtgt gctttgccac g                                                    21
```

-continued

```
SEQ ID NO: 5              moltype = DNA  length = 18
FEATURE                   Location/Qualifiers
misc_feature              1..18
                          note = Reverse primer
source                    1..18
                          mol_type = other DNA
                          organism = synthetic construct
SEQUENCE: 5
gtgcgaatac ctcggacc                                                       18

SEQ ID NO: 6              moltype = DNA  length = 39
FEATURE                   Location/Qualifiers
misc_feature              1..39
                          note = Exemplary 5' adapter
modified_base             12..17
                          mod_base = OTHER
                          note = Between 1 and 6 nucleotides in positions 12 to 17
                           can beLNA-enhanced
misc_difference           12..17
                          note = Between 1 and 6 nucleotides in positions 12 to 17
                           can beLNA-enhanced
modified_base             34..39
                          mod_base = OTHER
                          note = Between 1 and 6 nucleotides in positions 34 to 39
                           can beLNA-enhanced
misc_difference           34..39
                          note = Between 1 and 6 nucleotides in positions 34 to 39
                           can beLNA-enhanced
misc_feature              1..37
                          note = Bases are DNA
misc_feature              38..39
                          note = Bases are RNA
source                    1..39
                          mol_type = other DNA
                          organism = synthetic construct
SEQUENCE: 6
atctacgggt tcgtggcgtg gagtgtgtgc tttgccacg                                39

SEQ ID NO: 7              moltype = DNA  length = 40
FEATURE                   Location/Qualifiers
misc_feature              1..40
                          note = Exemplary 3' adapter
modified_base             1
                          mod_base = OTHER
                          note = This nucleotide is 5' terminally phosphorylated
misc_difference           1..8
                          note = Between 1 and 8 nucleotides in positions 1 to 8 can
                           beLNA-enhanced
modified_base             1..8
                          mod_base = OTHER
                          note = Between 1 and 8 nucleotides in positions 1 to 8 can
                           beLNA-enhanced
modified_base             25..32
                          mod_base = OTHER
                          note = Between 1 and 8 nucleotides in positions 25 to 32
                           can beLNA-enhanced
misc_difference           25..32
                          note = Between 1 and 8 nucleotides in positions 25 to 32
                           can beLNA-enhanced
modified_base             40
                          mod_base = OTHER
                          note = This nucleotide is a 3' inverted deoxynucleotide
source                    1..40
                          mol_type = other DNA
                          organism = synthetic construct
SEQUENCE: 7
ctcagtgcag ggtccgaggt attcgcactg agcacaagtt                               40

SEQ ID NO: 8              moltype = RNA  length = 22
FEATURE                   Location/Qualifiers
source                    1..22
                          mol_type = other RNA
                          organism = Homo sapiens
SEQUENCE: 8
aacccgtaga tccgaacttg tg                                                  22

SEQ ID NO: 9              moltype = RNA  length = 21
FEATURE                   Location/Qualifiers
source                    1..21
```

```
                          mol_type = other RNA
                          organism = Homo sapiens
SEQUENCE: 9
acccgtagat ccgaacttgt g                                            21

SEQ ID NO: 10             moltype = RNA   length = 23
FEATURE                   Location/Qualifiers
source                    1..23
                          mol_type = other RNA
                          organism = Homo sapiens
SEQUENCE: 10
aaacccgtag atccgaactt gtg                                          23

SEQ ID NO: 11             moltype = RNA   length = 21
FEATURE                   Location/Qualifiers
source                    1..21
                          mol_type = other RNA
                          organism = Homo sapiens
SEQUENCE: 11
aacccgtaga tccgaacttg t                                            21

SEQ ID NO: 12             moltype = RNA   length = 23
FEATURE                   Location/Qualifiers
source                    1..23
                          mol_type = other RNA
                          organism = Homo sapiens
SEQUENCE: 12
aacccgtaga tccgaacttg tgg                                          23

SEQ ID NO: 13             moltype = RNA   length = 22
FEATURE                   Location/Qualifiers
source                    1..22
                          mol_type = other RNA
                          organism = Homo sapiens
SEQUENCE: 13
aacgcgtaga tccgaacttg tg                                           22

SEQ ID NO: 14             moltype = RNA   length = 22
FEATURE                   Location/Qualifiers
source                    1..22
                          mol_type = other RNA
                          organism = Homo sapiens
SEQUENCE: 14
aacccgtaga tgcgaacttg tg                                           22

SEQ ID NO: 15             moltype = RNA   length = 22
FEATURE                   Location/Qualifiers
source                    1..22
                          mol_type = other RNA
                          organism = Homo sapiens
SEQUENCE: 15
aacccgtaga tccgaactag tg                                           22

SEQ ID NO: 16             moltype = DNA   length = 40
FEATURE                   Location/Qualifiers
misc_feature              1..40
                          note = 5' adapter DB-mir100-5A for ligation
modified_base             19
                          mod_base = OTHER
                          note = This nucleotide lack a base
misc_feature              1..38
                          note = Bases are DNA
misc_feature              39..40
                          note = Bases are RNA
source                    1..40
                          mol_type = other DNA
                          organism = synthetic construct
SEQUENCE: 16
atctacgggt tcgtggcgnt ggagtgtgtg ctttgccacg                        40

SEQ ID NO: 17             moltype = DNA   length = 40
FEATURE                   Location/Qualifiers
misc_feature              1..40
                          note = 5' adapter DB-mir100-5B for ligation
modified_base             19
                          mod_base = OTHER
                          note = This nucleotide lack a base
misc_feature              1..38
                          note = Bases are DNA
```

```
misc_feature            39..40
                        note = Bases are RNA
source                  1..40
                        mol_type = other DNA
                        organism = synthetic construct
SEQUENCE: 17
gatctacggg tcgtggcgnt ggagtgtgtg ctttgccacg                            40

SEQ ID NO: 18           moltype = DNA  length = 40
FEATURE                 Location/Qualifiers
misc_feature            1..40
                        note = 5' adapter DB-mir100-5D for ligation
modified_base           19
                        mod_base = OTHER
                        note = This nucleotide lack a base
misc_feature            1..38
                        note = Bases are DNA
misc_feature            39..40
                        note = Bases are RNA
source                  1..40
                        mol_type = other DNA
                        organism = synthetic construct
SEQUENCE: 18
tctacgggtt tcgtggcgnt ggagtgtgtg ctttgccacg                            40

SEQ ID NO: 19           moltype = DNA  length = 40
FEATURE                 Location/Qualifiers
misc_feature            1..40
                        note = 5' adapter DB-mir100-5E for ligation
modified_base           19
                        mod_base = OTHER
                        note = This nucleotide lack a base
misc_feature            1..38
                        note = Bases are DNA
misc_feature            39..40
                        note = Bases are RNA
source                  1..40
                        mol_type = other DNA
                        organism = synthetic construct
SEQUENCE: 19
atctacgcgt tcgtggcgnt ggagtgtgtg ctttgccacg                            40

SEQ ID NO: 20           moltype = DNA  length = 40
FEATURE                 Location/Qualifiers
misc_feature            1..40
                        note = 3' adapter DB-mir100-3Z for ligation
modified_base           1
                        mod_base = OTHER
                        note = This nucleotide is 5' terminally phosphorylated
modified_base           40
                        mod_base = OTHER
                        note = This nucleotide is a 3' inverted deoxynucleotide
source                  1..40
                        mol_type = other DNA
                        organism = synthetic construct
SEQUENCE: 20
ctcagtgcag ggtccgaggt attcgcactg agcacaagtt                            40

SEQ ID NO: 21           moltype = DNA  length = 40
FEATURE                 Location/Qualifiers
misc_feature            1..40
                        note = 3' adapter DB-mir100-3X for ligation
modified_base           1
                        mod_base = OTHER
                        note = This nucleotide is 5' terminally phosphorylated
modified_base           40
                        mod_base = OTHER
                        note = This nucleotide is a 3' inverted deoxynucleotide
source                  1..40
                        mol_type = other DNA
                        organism = synthetic construct
SEQUENCE: 21
ctcagtgcag ggtccgaggt attcgcactg agacaagttt                            40

SEQ ID NO: 22           moltype = DNA  length = 40
FEATURE                 Location/Qualifiers
misc_feature            1..40
                        note = 3' adapter DB-mir100-3S for ligation
modified_base           1
```

```
                        mod_base = OTHER
                        note = This nucleotide is 5' terminally phosphorylated
modified_base           40
                        mod_base = OTHER
                        note = This nucleotide is a 3' inverted deoxynucleotide
source                  1..40
                        mol_type = other DNA
                        organism = synthetic construct
SEQUENCE: 22
ctcagtgcag ggtccgaggt attcgcactg agccacaagt                                 40

SEQ ID NO: 23           moltype = DNA   length = 40
FEATURE                 Location/Qualifiers
misc_feature            1..40
                        note = 3' adapter DB-mir100-3T for ligation
modified_base           1
                        mod_base = OTHER
                        note = This nucleotide is 5' terminally phosphorylated
modified_base           40
                        mod_base = OTHER
                        note = This nucleotide is a 3' inverted deoxynucleotide
source                  1..40
                        mol_type = other DNA
                        organism = synthetic construct
SEQUENCE: 23
ctcagtgcag ggtccgaggt attcgcactg agcactagtt                                 40

SEQ ID NO: 24           moltype = DNA   length = 20
FEATURE                 Location/Qualifiers
misc_feature            1..20
                        note = Taqman probe DB-mir100-K
modified_base           1
                        mod_base = OTHER
                        note = Labelled with 5' 6-FAM (fluorescein)
modified_base           9..10
                        mod_base = OTHER
                        note = These two nucleotides are connected by an internal
                         ZEN(TM)quencher proprietary to Integrated DNA Technologies
                         Inc.
modified_base           20
                        mod_base = OTHER
                        note = Labelled with Iowa black fluorescein quencher
source                  1..20
                        mol_type = other DNA
                        organism = synthetic construct
SEQUENCE: 24
acgaacccgt agatccgaac                                                       20

SEQ ID NO: 25           moltype = DNA   length = 20
FEATURE                 Location/Qualifiers
misc_feature            1..20
                        note = Taqman probe DB-mir100-L
modified_base           1
                        mod_base = OTHER
                        note = Labelled with 5' 6-FAM (fluorescein)
modified_base           9..10
                        mod_base = OTHER
                        note = These two nucleotides are connected by an internal
                         ZEN(TM)quencher proprietary to Integrated DNA Technologies
                         Inc.
modified_base           20
                        mod_base = OTHER
                        note = Labelled with Iowa black fluorescein quencher
source                  1..20
                        mol_type = other DNA
                        organism = synthetic construct
SEQUENCE: 25
acgacccgta gatccgaact                                                       20

SEQ ID NO: 26           moltype = DNA   length = 20
FEATURE                 Location/Qualifiers
misc_feature            1..20
                        note = DB-mir100-P
modified_base           1
                        mod_base = OTHER
                        note = Labelled with 5' 6-FAM (fluorescein)
modified_base           9..10
                        mod_base = OTHER
                        note = These two nucleotides are connected by an internal
```

|     |     |
| --- | --- |
| | ZEN(TM)quencher proprietary to Integrated DNA Technologies Inc. |
| modified_base | 20 |
| | mod_base = OTHER |
| | note = Labelled with Iowa black fluorescein quencher |
| source | 1..20 |
| | mol_type = other DNA |
| | organism = synthetic construct |
| SEQUENCE: 26 | |
| acgaaacccg tagatccgaa | 20 |
| | |
| SEQ ID NO: 27 | moltype = DNA   length = 20 |
| FEATURE | Location/Qualifiers |
| misc_feature | 1..20 |
| | note = Taqman probe DB-mir100-Q |
| modified_base | 1 |
| | mod_base = OTHER |
| | note = Labelled with 5' 6-FAM (fluorescein) |
| modified_base | 9..10 |
| | mod_base = OTHER |
| | note = These two nucleotides are connected by an internal ZEN(TM)quencher proprietary to Integrated DNA Technologies Inc. |
| modified_base | 20 |
| | mod_base = OTHER |
| | note = Labelled with Iowa black fluorescein quencher |
| source | 1..20 |
| | mol_type = other DNA |
| | organism = synthetic construct |
| SEQUENCE: 27 | |
| acgaacgcgt agatccgaac | 20 |
| | |
| SEQ ID NO: 28 | moltype = DNA   length = 20 |
| FEATURE | Location/Qualifiers |
| misc_feature | 1..20 |
| | note = Taqman probe DB-mir100-R |
| modified_base | 1 |
| | mod_base = OTHER |
| | note = Labelled with 5' 6-FAM (fluorescein) |
| modified_base | 9..10 |
| | mod_base = OTHER |
| | note = These two nucleotides are connected by an internal ZEN(TM)quencher proprietary to Integrated DNA Technologies Inc. |
| modified_base | 20 |
| | mod_base = OTHER |
| | note = Labelled with Iowa black fluorescein quencher |
| source | 1..20 |
| | mol_type = other DNA |
| | organism = synthetic construct |
| SEQUENCE: 28 | |
| acgaacccgt agatgcgaac | 20 |
| | |
| SEQ ID NO: 29 | moltype = DNA   length = 44 |
| FEATURE | Location/Qualifiers |
| misc_feature | 1..44 |
| | note = 5' adapter with idSp |
| variation | 1..9 |
| | note = n is a c g t or u |
| misc_difference | 1..9 |
| | note = Positions may be absent |
| variation | 10..15 |
| | note = n is a c g t or u |
| modified_base | 16..21 |
| | mod_base = OTHER |
| | note = Between 1 and 6 nucleotides in positions 16 to 21 can beLNA-enhanced |
| misc_difference | 16..21 |
| | note = Between 1 and 6 nucleotides in positions 16 to 21 can beLNA-enhanced |
| modified_base | 23 |
| | mod_base = OTHER |
| | note = This nucleotide lack a base |
| modified_base | 39..44 |
| | mod_base = OTHER |
| | note = Between 1 and 6 nucleotides in positions 39 to 44 can beLNA-enhanced |
| misc_difference | 39..44 |
| | note = Between 1 and 6 nucleotides in positions 39 to 44 |

```
                        can beLNA-enhanced
misc_feature            1..38
                        note = Bases are DNA
misc_feature            43..44
                        note = Bases are RNA
source                  1..44
                        mol_type = other DNA
                        organism = synthetic construct
SEQUENCE: 29
nnnnnnnnnn nnnnncgtgg cgntggagtg tgtgctttgc cacg                    44
```